(12) United States Patent
Alburty et al.

(10) Patent No.: US 8,726,744 B2
(45) Date of Patent: May 20, 2014

(54) PORTABLE CONCENTRATOR

(75) Inventors: David Scott Alburty, Drexel, MO (US); Andrew Edward Page, Smithton, MO (US); Alec D. Adolphson, Raymore, MO (US); Zachary A. Packingham, Drexel, MO (US)

(73) Assignee: InnovaPrep LLC, Drexel, MO (US)

( * ) Notice: Subject to any disclaimer, the term of this patent is extended or adjusted under 35 U.S.C. 154(b) by 421 days.

(21) Appl. No.: 13/028,897

(22) Filed: Feb. 16, 2011

(65) Prior Publication Data

US 2011/0197685 A1 Aug. 18, 2011

Related U.S. Application Data

(60) Provisional application No. 61/338,051, filed on Feb. 16, 2010.

(51) Int. Cl.
*G01N 1/22* (2006.01)
*G01N 1/00* (2006.01)
*G01N 1/04* (2006.01)

(52) U.S. Cl.
USPC .... 73/863.23; 73/28.04; 73/64.56; 73/864.71

(58) Field of Classification Search
USPC .......... 73/28.04, 61.71, 61.72, 64.56, 863.23, 73/864.71
See application file for complete search history.

(56) References Cited

U.S. PATENT DOCUMENTS

| | | | | |
|---|---|---|---|---|
| 7,530,258 B2 * | 5/2009 | Bremer et al. | | 73/23.41 |
| 7,776,615 B2 * | 8/2010 | Yuka et al. | | 436/178 |
| 2005/0150841 A1 * | 7/2005 | Ferguson | | 210/741 |
| 2007/0113616 A1 * | 5/2007 | Schilling et al. | | 73/23.41 |
| 2008/0064115 A1 * | 3/2008 | Hiramatsu et al. | | 436/178 |
| 2009/0241644 A1 * | 10/2009 | Bonfiglioli | | 73/49.3 |

FOREIGN PATENT DOCUMENTS

JP 2000146933 A * 5/2000 ............. G01N 30/32

* cited by examiner

*Primary Examiner* — Hezron E Williams
*Assistant Examiner* — Nathaniel Kolb
(74) *Attorney, Agent, or Firm* — Moazzam & Associates, LLC

(57) ABSTRACT

The present disclosure provides devices, systems and methods for concentrating a fluid sample. A portable or hand-held concentrator is used to draw the fluid sample through a filter into an internal chamber, capturing target particles on the filter. An elution cartridge containing an elution fluid is used to recover the captured particles into a reduced fluid volume. The hand-held concentrator includes a tip, which, when opened, allows the hand-held concentrator to draw the fluid sample into the tip and through the filter wall into the internal chamber. The drawing occurs due to a vacuum or wicking source in the internal chamber of the hand-held concentrator. The target particles are captured on the filter. The elution fluid contains a foaming agent and is held under a head pressure of gas soluble in the elution fluid. The target particles are eluted from the filter into the reduced fluid volume using an elution foam that is formed when the elution fluid is released from the elution cartridge. Embodiments of the hand-held concentrator are entirely self-contained and can operate without electrical power.

15 Claims, 23 Drawing Sheets

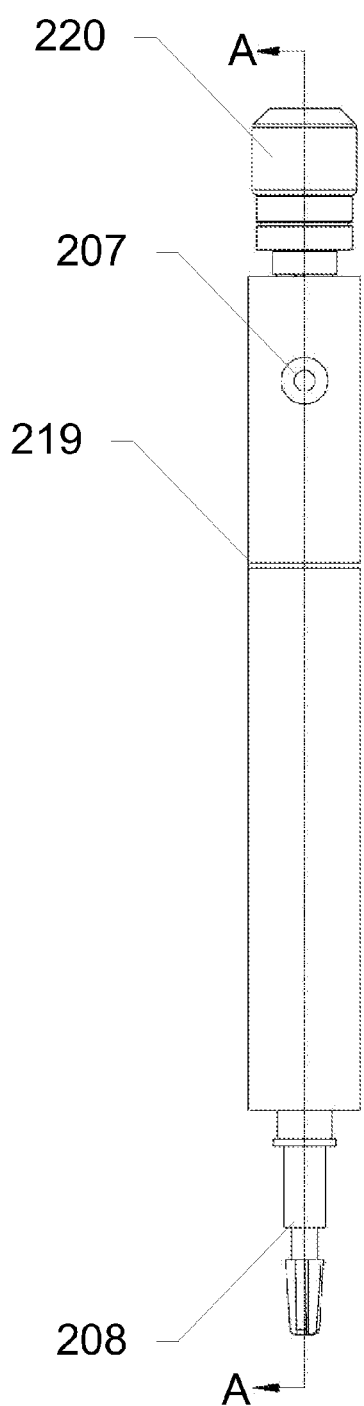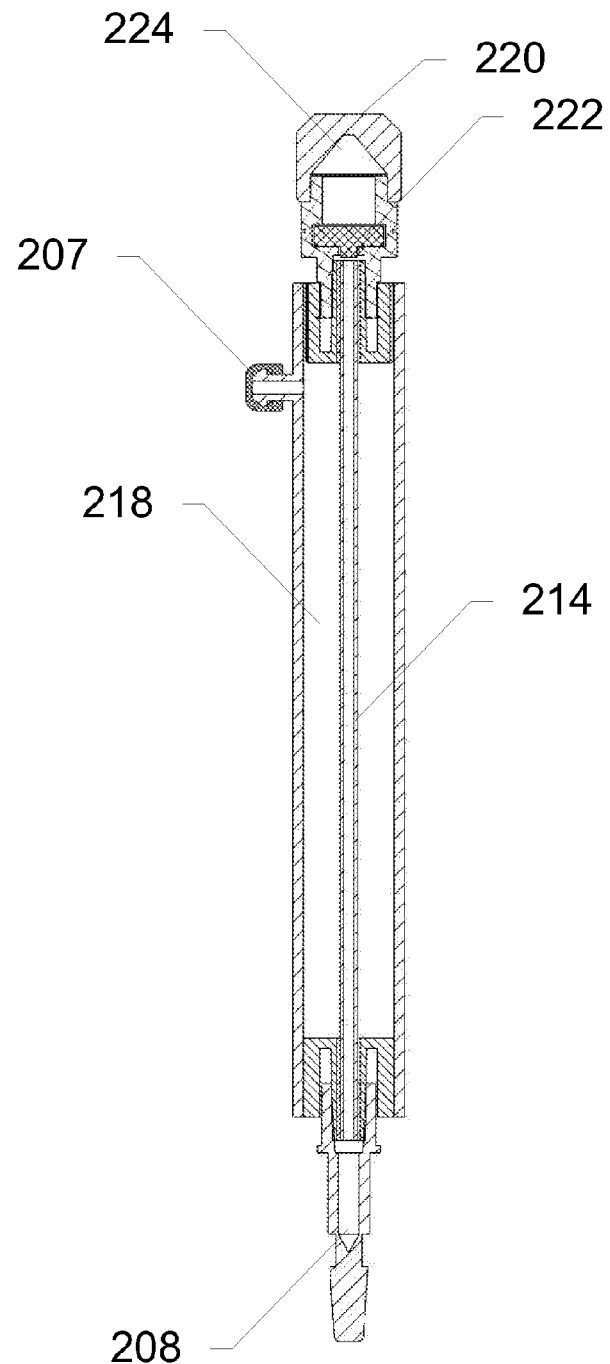
FIG. 2B       FIG. 2C

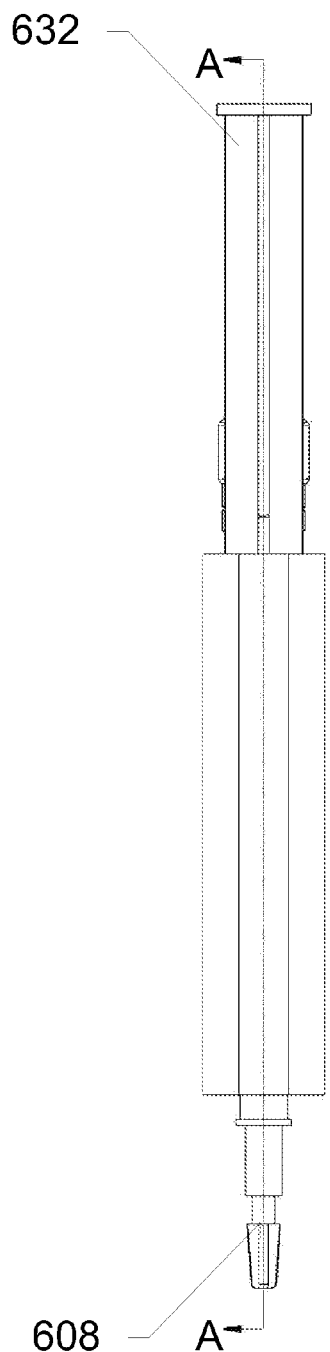
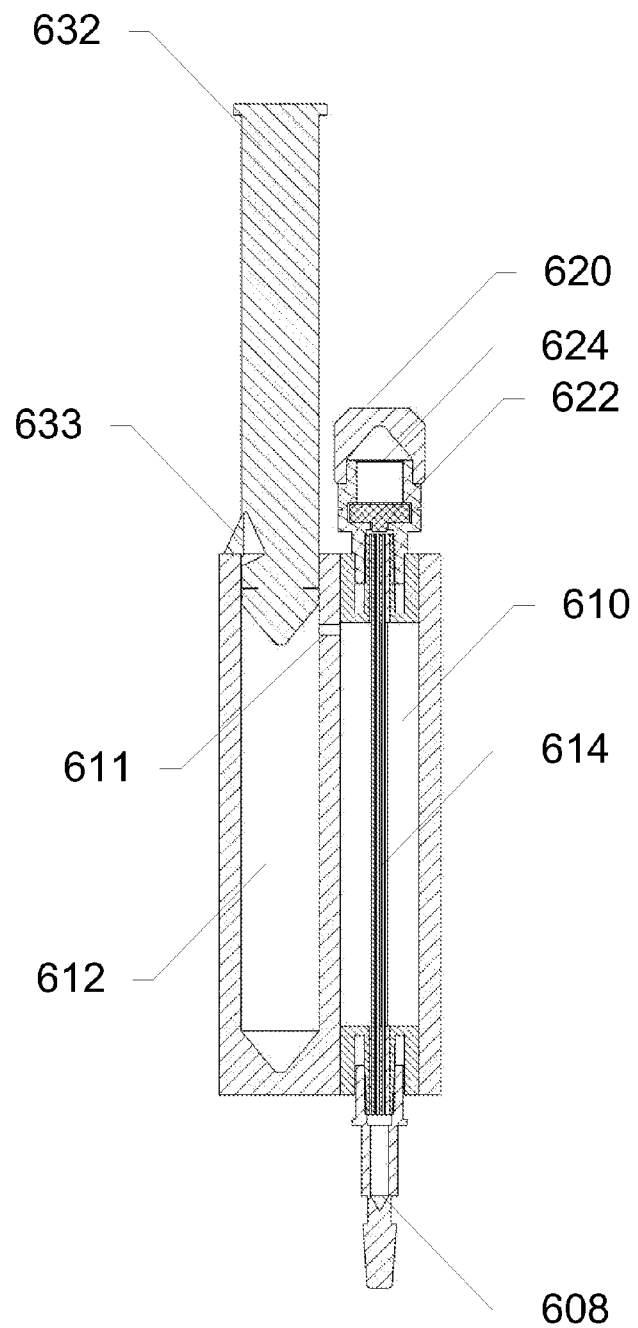
FIG. 6B  FIG. 6C

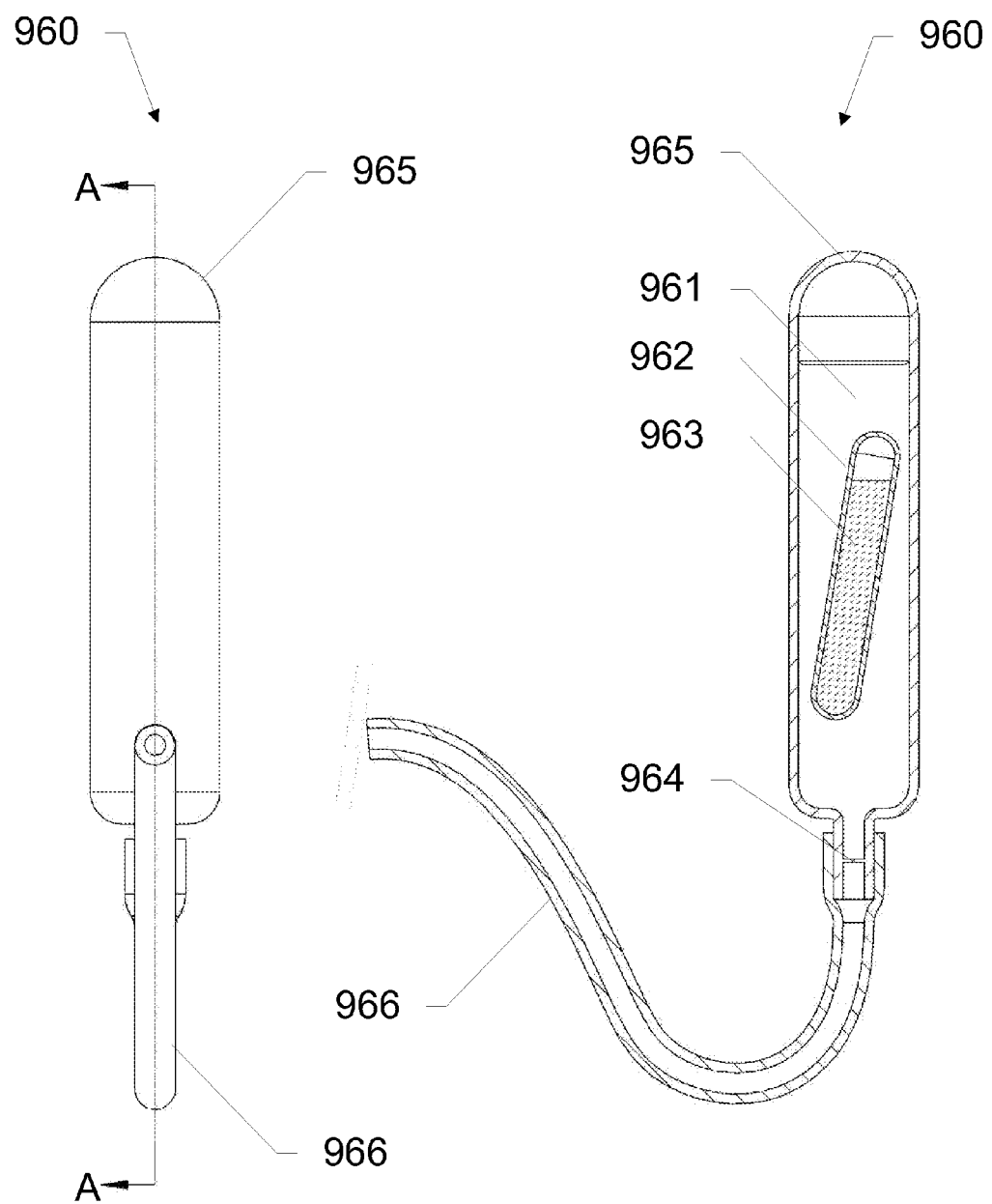
FIG. 9B  FIG. 9C

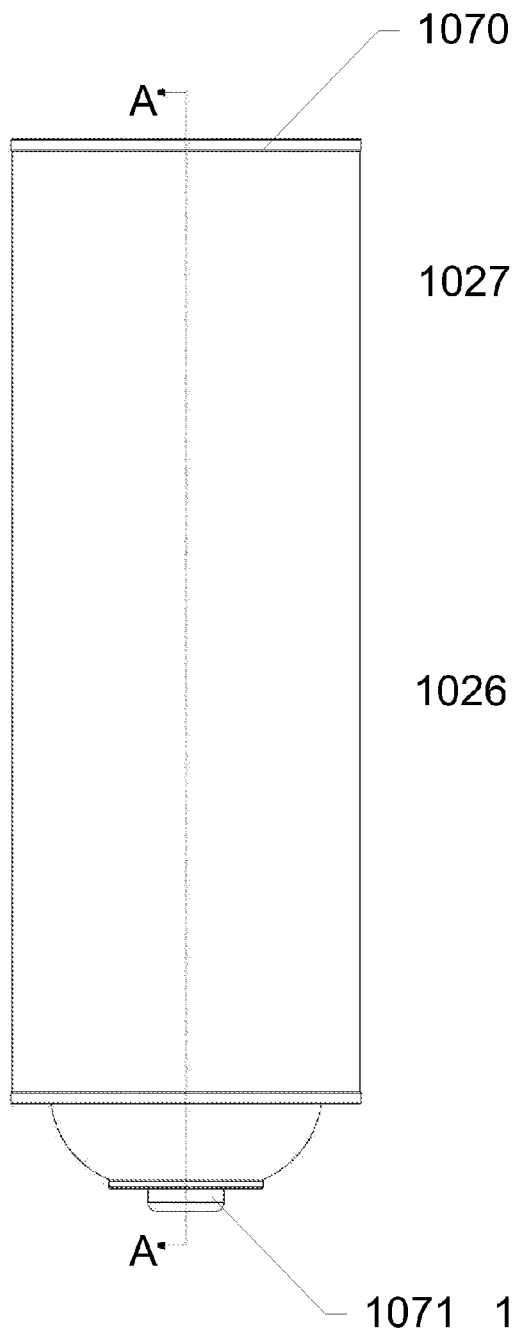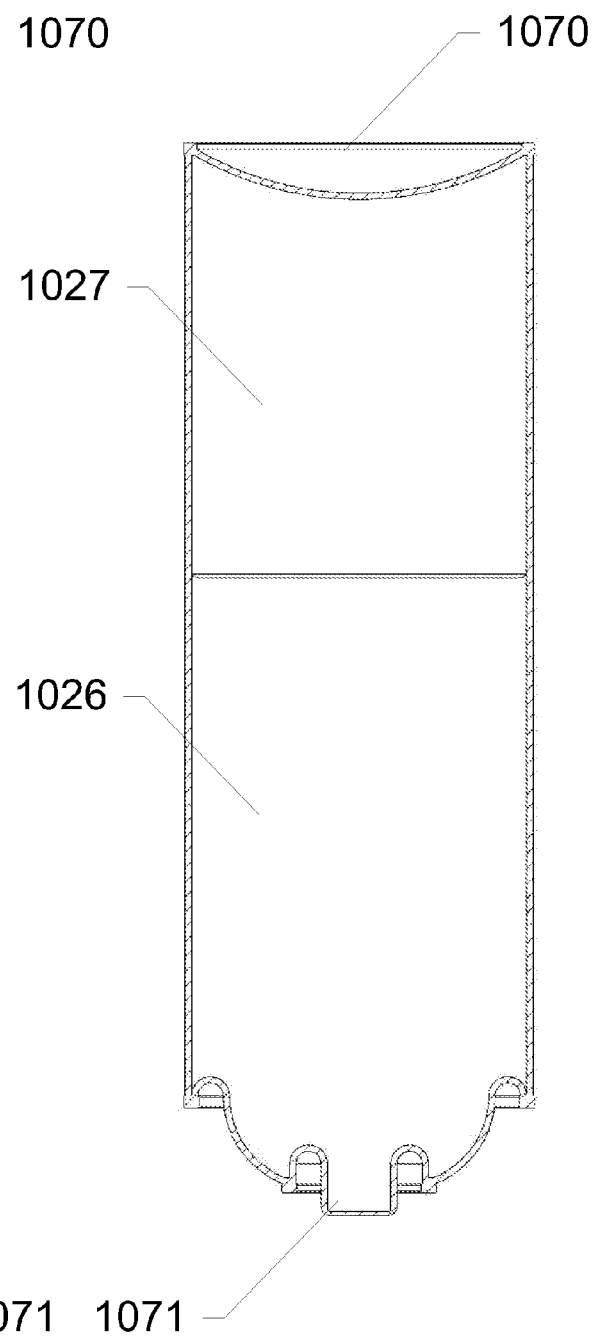
FIG. 10B  FIG. 10C

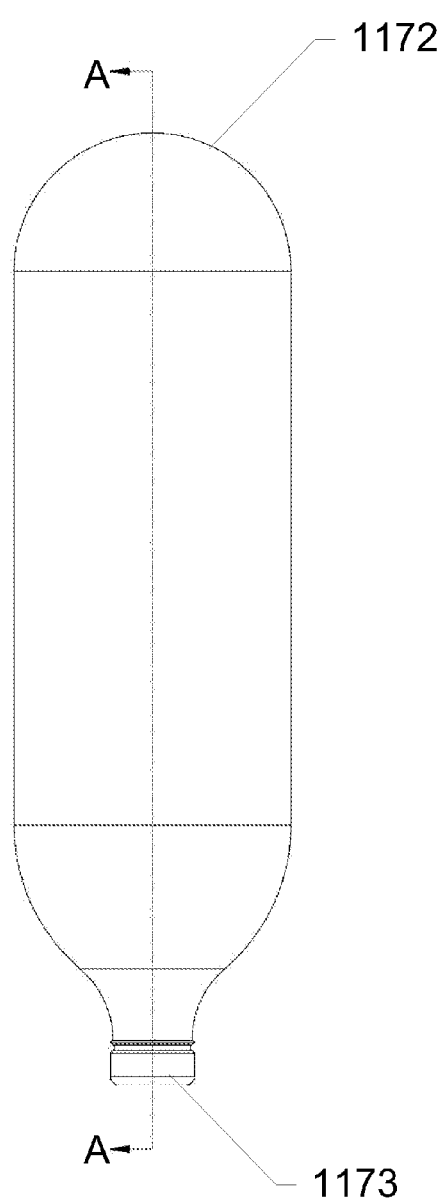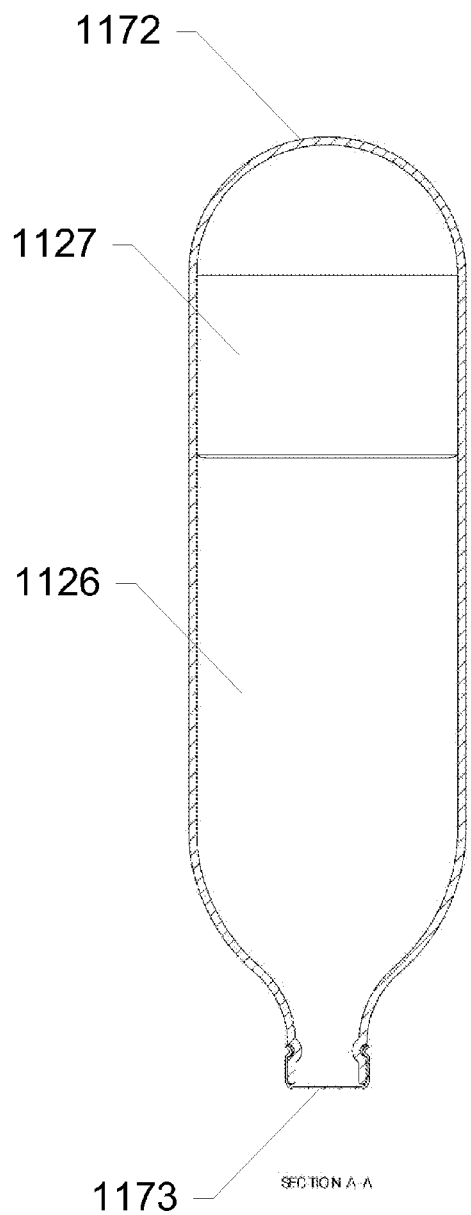
FIG. 11B  FIG. 11C

PORTABLE CONCENTRATOR

This U.S. patent application claims priority to U.S. Provisional Patent Application Ser. No. 61/338,051, filed Feb. 16, 2010, the content of which is hereby incorporated by reference herein in its entirety into this disclosure.

BACKGROUND OF THE INVENTION

1. Field of the Invention

The invention relates generally to the field of sample preparation. More particularly, the invention relates to methods, systems and devices for concentrating a substance within a fluid sample.

2. Background of the Invention

The difficulties of detecting and quantifying particles in air and liquids are well known. Existing systems all begin to fail as concentration falls away until eventually, with diminished concentrations of analyte, there is an inability to detect at all. This poses a significant problem for national security where, for example, the postal anthrax attacks of 2001 and the subsequent war on terrorism have revealed shortcomings in the sampling and detection of biothreats. The medical arts are similarly affected by the existing limits on detection, as are the environmental sciences.

In the fields of biodefense and aerosol research it is common to collect aerosols into a liquid sample using a wet cyclone or similar device. The aerosol is collected into an aqueous sample so that subsequent analysis of biological particles can be performed using standard techniques that primarily require that the sample be contained in liquid. These "wet" collectors have many failings, including: difficulty in maintaining a set fluid volume, difficulties with buildup of particle matter in the device, and requirements for storage of the fluid in varying environmental conditions.

Dry filters have long been used for collection of aerosols, as well as for collection of particles from liquids. However, dry filters fail primarily for the use of identifying biological particles because detectors generally require a liquid sample and it is extremely difficult to remove the particles into a liquid. Methods for removing particles from flat filters are common but are tedious, inefficient, and require large liquid volumes.

Concentration of particles from a liquid is traditionally performed using centrifugation. Centrifugal force is used for the separation of mixtures according to differences in the density of the individual components present in the mixture. This force separates a mixture forming a pellet of relatively dense material at the bottom of the tube. The remaining solution, referred to as the supernate or supernatant liquid, may then be carefully decanted from the tube without disturbing the pellet, or withdrawn using a Pasteur pipette. The rate of centrifugation is specified by the acceleration applied to the sample, and is typically measured in revolutions per minute (RPM) or g-forces. The particle settling velocity in centrifugation is a function of the particle's size and shape, centrifugal acceleration, the volume fraction of solids present, the density difference between the particle and the liquid, and viscosity of the liquid.

Problems with the centrifugation technique limit its applicability. The settling velocity of particles in the micron size range is quite low. Consequently, centrifugal concentration of these particles takes several minutes to several hours. The actual time varies depending on the volume of the sample, the equipment used, and the skill of the operator.

Centrifugation techniques are tedious in that they are normally made up of multiple steps each requiring a high level of concentration from the operator. Most microbiology laboratories process large numbers of samples by centrifugation on a daily basis. The potential for human error is high due to the tedious nature and automation of these techniques is difficult and costly. Centrifugation also generally requires powered equipment. Thus, many situations, such as emergency response, prevent their use.

Other concentration techniques have been explored and primarily fall into three technology groups—microfluidic/electrophoretic based, filtration based, and capture based. However, each of these techniques has disadvantages that prevent their use in certain situations.

What is needed is a single device for concentrating a fluid sample. Such a device should be able to operate without electrical power to enable use in diverse situations.

SUMMARY OF THE INVENTION

The present invention provides devices, systems and methods for concentrating a fluid sample. A portable or hand-held concentrator is used to draw the fluid sample through a filter into an internal chamber, capturing target particles on the filter. An elution cartridge containing an elution fluid is used to recover the captured particles into a reduced fluid volume. The hand-held concentrator includes a tip, which, when opened, allows the hand-held concentrator to draw the fluid sample into the tip and through the filter wall into the internal chamber. The drawing occurs due to a vacuum or wicking source in the internal chamber of the hand-held concentrator. The target particles are captured on the filter. The elution fluid contains a foaming agent and is held under a head pressure of gas soluble in the elution fluid. The target particles are eluted from the filter into the reduced fluid volume using an elution foam that is formed when the elution fluid is released from the elution cartridge. Embodiments of the hand-held concentrator are entirely self-contained and can operate without electrical power.

Use of the hand-held concentrator may be initiated by placing the tip in a container with the fluid sample. The tip is pressed against the bottom of the sample container and broken off, allowing the vacuum stored in an internal chamber of the hand-held concentrator to draw the fluid sample into a retentate portion of the internal chamber, through the filter, and into the permeate portion of the internal chamber. As the fluid sample is pulled through the filter, target particles are captured in the inside bore or retentate side of the filter, while liquids and solutions pass through the fiber wall into the permeate portion of the internal chamber. Once the internal chamber has sufficiently filled with liquid, the tip is removed from the sample container and the remaining fluid in the tip and on the retentate side of the filter is allowed to be drawn through to the permeate portion of the internal chamber. A valve on an elution cartridge is then activated, allowing an elution foam to be released and pushed tangentially to the filter surface, recovering the captured particles and dispensing them out of the tip in a reduced volume.

In one exemplary embodiment, the present invention is a device for concentrating target particles from a fluid sample. The device includes an internal chamber; a filter within the internal chamber creating a retentate portion of the internal chamber and a permeate portion of the internal chamber, the filter having a porous surface; a tip in fluid communication with the retentate portion of the internal chamber; and a drawing source within the internal chamber. The fluid sample is drawn by the drawing source into the tip and the retentate portion of the internal chamber, through the filter, and into the permeate portion of the internal chamber. Target particles within the fluid sample are captured by the filter.

In another exemplary embodiment, the present invention is a method for concentration of target particles from a fluid sample. The method includes placing a tip of a hand-held concentrator in the fluid sample; opening the tip; drawing the fluid sample into the tip, through a filter, and into an internal chamber of the hand-held concentrator; and capturing target particles from the fluid sample on the filter. The fluid sample is drawn via a vacuum in the internal chamber.

In yet another exemplary embodiment, the present invention is a system for concentrating target particles from a fluid sample. The system includes a hand-held concentrator, the hand-held concentrator including an internal chamber, a filter within the internal chamber creating a retentate portion of the internal chamber and a permeate portion of the internal chamber, a tip in fluid communication with the retentate portion of the internal chamber, a drawing source within the internal chamber; and an elution cartridge coupled to the hand-held concentrator. The hand-held concentrator draws the fluid sample into the tip, through the retentate portion, and through the filter, capturing the target particles on the filter. The elution cartridge is manipulated to elute the target particles from the filter.

BRIEF DESCRIPTION OF THE DRAWINGS

FIGS. 2A-C show a hand-held concentrator (HHC) utilizing a single internal chamber, according to an exemplary embodiment of the present invention.

FIGS. 6A-C show a hand-held concentrator including a syringe, according to an exemplary embodiment of the present invention.

FIGS. 9A-C show an elution cartridge, according to an exemplary embodiment of the present invention.

FIGS. 10A-C show an elution cartridge, according to an exemplary embodiment of the present invention.

FIGS. 11A-C show an elution cartridge, according to an exemplary embodiment of the present invention.

DETAILED DESCRIPTION OF THE INVENTION

Figure 1A:
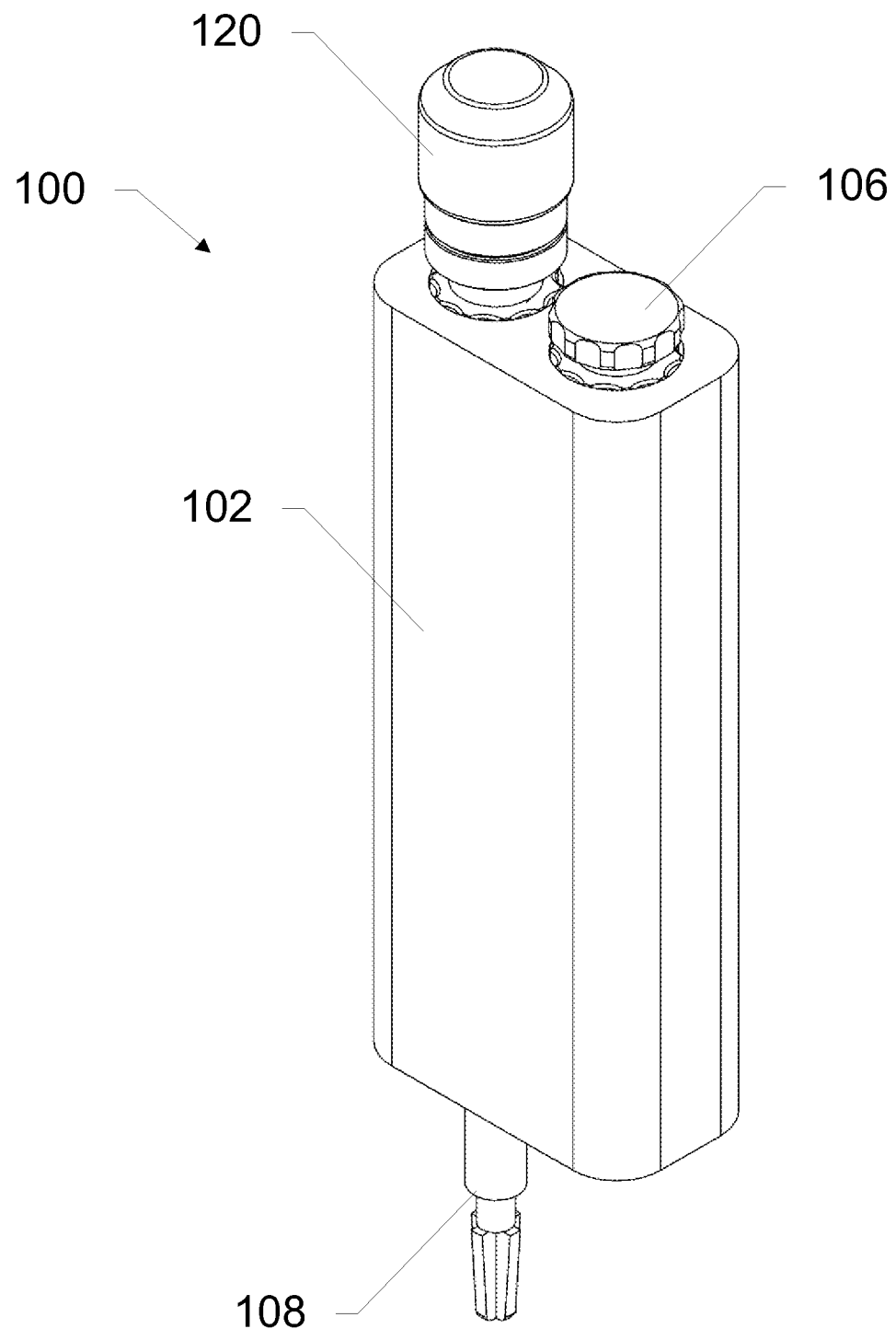
FIGS. 1A-C show a hand-held concentrator (HHC), according to an exemplary embodiment of the present invention.

The present invention discloses a portable or hand-held concentrator (HHC) for concentrating a fluid sample. A portable or hand-held concentrator is used to draw the fluid sample through a filter into an internal chamber, capturing target particles on the filter. An elution cartridge containing an elution fluid is used to recover the captured particles into a reduced fluid volume. The hand-held concentrator includes a tip, which, when opened, allows the hand-held concentrator to draw the fluid sample into the tip and through the filter wall into the internal chamber. The drawing occurs due to a vacuum or wicking source in the internal chamber of the hand-held concentrator. The target particles are captured on the filter. The elution fluid contains a foaming agent and is held under a head pressure of gas soluble in the elution fluid. The target particles are eluted from the filter into the reduced fluid volume using an elution foam that is formed when the elution fluid is released from the elution cartridge. Embodiments of the hand-held concentrator are entirely self-contained and can operate without electrical power.

Use of the hand-held concentrator may be initiated by placing the tip in a container with the fluid sample. The tip is pressed against the bottom of the sample container and broken off, allowing the vacuum stored in an internal chamber of the hand-held concentrator to draw the fluid sample into a retentate portion of the internal chamber, through the filter, and into the permeate portion of the internal chamber. As the fluid sample is pulled through the filter, target particles are captured in the inside bore or retentate side of the filter, while liquids and solutions pass through the fiber wall into the permeate portion of the internal chamber. Once the internal chamber has sufficiently filled with liquid, the tip is removed from the sample container and the remaining fluid in the tip and on the retentate side of the filter is allowed to be drawn through to the permeate portion of the internal chamber. A valve on an elution cartridge is then activated, allowing an elution foam to be released and pushed tangentially to the filter surface, recovering the captured particles and dispensing them out of the tip in a reduced volume.

The present invention draws particular utility from its ability to be relatively compact and its ability to operate without electrical power. This enables the present invention to be used, for instance, in disaster situations or third-world countries, where there may not be any power and only limited resources available. The present invention may be used for on-site clinical analysis for first responder applications, tactical military operations, autonomous robotic operations, etc. The present invention may be used, for instance, to test water such as drinking, wash, recreational, and other types of water for ecoli and other contaminants, as well as clinical diagnostic sampling such as blood, semen, stool, etc.

After being dispensed, the concentrated sample may be further concentrated prior to analysis by immunomagnetic separation, solid phase extraction, electrophoretic or dielectrophoretic separation techniques, or other microfluidic concentration techniques. Generally, these techniques are useful only for smaller volumes, and are prohibitively costly or slow when performed on large volumes. However, the disclosed hand-held concentrator rapidly performs an initial concentration and reduces the sample volume to a volume that is more readily handled with these known techniques.

It is further possible to apply additional sample preparation techniques to the concentrated sample once dispensed. Additional sample preparation techniques include various methods of cell lysis, washing steps, inhibitor or interferent removal techniques, and labeling steps. Reduction of the sample volume prior to performing these techniques routinely improves the speed, efficiency, and cost of performing these sample preparation techniques.

Analysis of the concentrated sample may be performed with any number of commonly used traditional analytical or microbiological analysis methods or rapid analysis techniques, including rapid microbiological techniques. Analytical techniques of special interest include conventional methods of plating and enumeration, most probable number, immunoassay methods, polymerase chain reaction (PCR), electrochemical, microarray, flow cytometry, biosensors, lab-on-a-chip, and rapid growth based detection technologies.

The present invention further may be integrated into a fluidic manifold containing a number of pre-preparation, post-preparation, and analysis components, along with the hand-held concentrator. Prefiltration or pretreatment of the input sample may be used prior to delivery of the sample to the integrated fluidic manifold or may take place within this system. The vacuum or wicking source within the device may be used to draw the sample through pretreatment steps and the capture filter. Elution of the capture filter may then push the concentrated sample into the next sample preparation steps and onto the analysis steps. This combined approach may be implemented for point-of-care clinical diagnostic applications and a number of environmental and food safety applications as well as biodefense and other applications.

The present invention further enables concentrating microorganisms, including pathogens and spoilage organisms, from any number of beverages, including fruit juices, vegetable juices, carbonated beverages, alcoholic beverages and from homogenates or liquid samples produced from solid foods. By concentrating large sample volumes in the range of 10 mL to 10 L or more prior to analysis, it is possible to rapidly detect microorganisms at levels that were previously only detectable following lengthy culturing of a portion of the sample.

The disclosed HHC further enables testing samples resulting from manual swabbing of surfaces onto wetted swabs, pads, or pieces of filter material often taken for bioterrorism security monitoring. The samples are typically extracted into a volume of liquid resulting in a 2 to 20 mL volume initial sample. Samples like these may be quickly concentrated to much smaller volumes in the range of 4-400 µL such that agents may more easily be detected. In still other aspects, samples may be concentrated for water sampling in search of bioterrorism agents, or in the interest of public health and safety, especially where a sample may contain target agent(s) that are thought to be a threat to the health of humans, animals, or plants, causing societal disruption and economic harm. Agricultural products and livestock environments may also be evaluated by the instruments disclosed herein.

Environmental studies may also benefit from the present invention. These techniques include many types of sampling and analysis, such as assessing health effects through research regarding various materials in inhaled particulate matter with aerodynamic diameter below 2.5 microns (PM 2.5), or high altitude aerosol research, where low quantities of particulate are collected and must be concentrated for study. The present invention may further benefit clean rooms where very low aerosol concentrations of aerosol particles are collected for monitoring that is aimed at source control.

Forensic sciences may also benefit from the present invention by allowing for detection of DNA collected from large surfaces, articles of clothing, air samples, liquids or other forensic type samples. Touch DNA and low-template DNA techniques can be further extended by concentrating large sample volumes into volumes more closely matching the analysis volume. These types of sampling and analysis are advantageously performed for the fields of homeland security, corporate security, and military force protection.

Additional potential applications for the present invention include medical research and diagnostics. For example, sample concentration is useful in determining if catheter or other medical devices are contaminated with bacteria. These devices routinely become contaminated in the hospital setting. However it is often difficult to determine which device is causing an infection. Concentration of wash fluid from these devices allows for rapid detection of the infecting organism. Sample concentration is useful in cancer research where very low concentrations of experimental drugs in body fluids or urine are the targets of analysis and in allergy diagnosis where low quantities of specific antigens are the targets of analysis in body fluids. Health effects research may also benefit by determining health effects known to be caused by various materials in inhaled particulate matter with aerodynamic diameter below 2.5 microns (PM 2.5). Benefit is seen in the field of forensic medicine where low concentrations of DNA, toxins, or venoms are the targets of analysis in body fluids. Other aspects of use include the study of operating rooms for surface extraction and air monitoring of pathogens, as well as pharmaceutical manufacturing where the biological aerosol particulate matter concentration is regulated by the United States Food and Drug Administration.

For the following description, it can be assumed that most correspondingly labeled structures across the figures (e.g., 108 and 208, etc.) possess the same characteristics and are subject to the same structure and function. If there is a difference between correspondingly labeled elements that is not pointed out, and this difference results in a non-corresponding structure or function of an element for a particular embodiment, then that conflicting description given for that particular embodiment shall govern.

In the following figures, there will be shown and described multiple configurations of hand-held concentrators which may be used to concentrate biological particles into a reduced liquid volume. Because the sample is aspirated, concentrated, and dispensed with a single instrument, work flow is improved and the required operator skill level is significantly reduced.

Figures 1B, 1C:
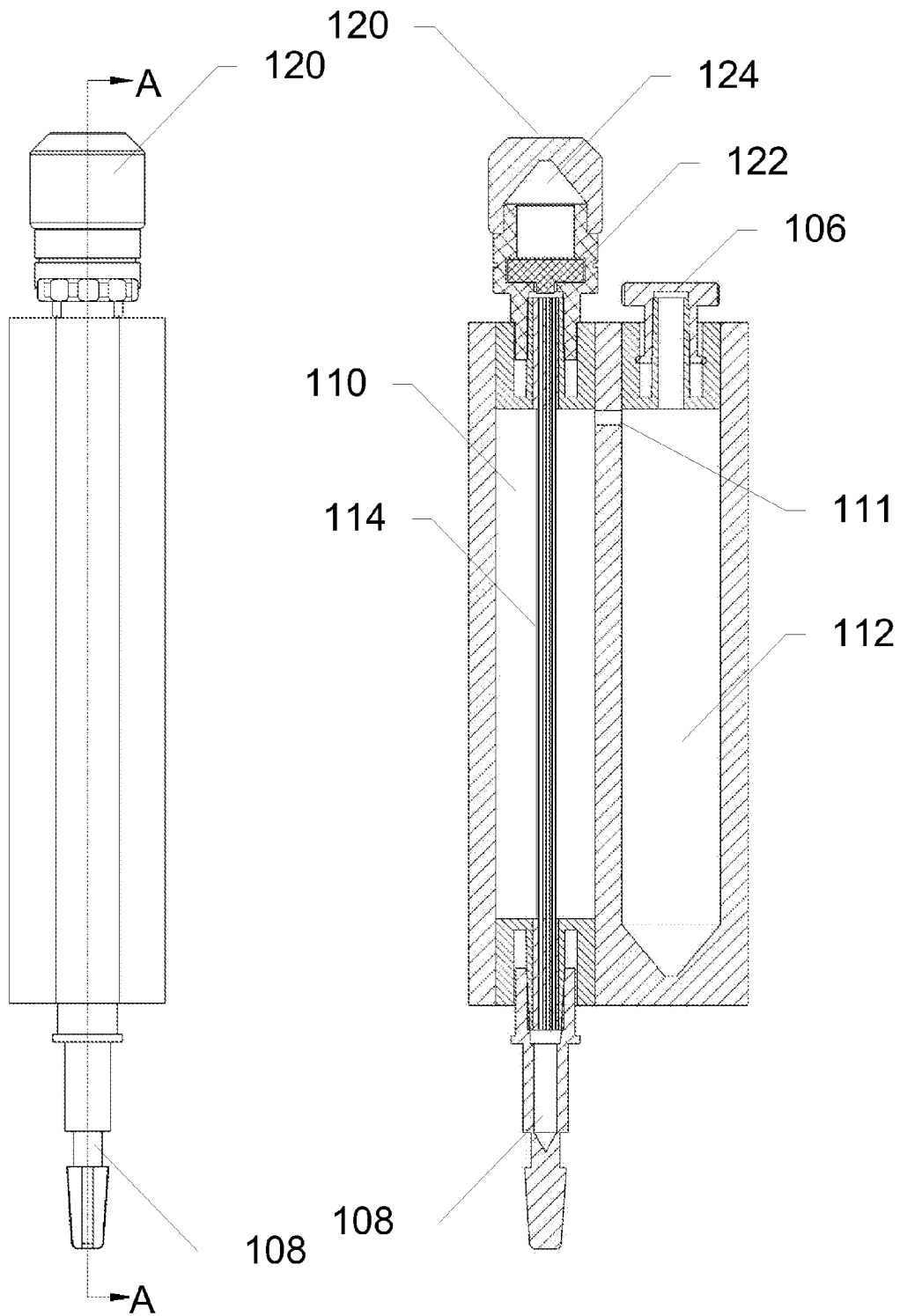

FIG. 1A shows a hand-held concentrator (HHC) 100, according to an exemplary embodiment of the present invention. In this embodiment, HHC 100 is a self-contained vacuum-based device. HHC 100 includes a HHC body 102, an evacuation port 106, a tip 108, and an elution cartridge 120. HHC body 102 encloses two internal chambers 110 and 112, as seen in FIG. 1C. HHC body 102 is preferably transparent, such that a user can see the volume of a fluid sample collected. Evacuation port 106 contains a valve to draw air out of the internal chambers to introduce a vacuum within the internal chambers. Evacuation port 106 is preferably self-sealing in order to hold the vacuum in the internal chambers. Tip 108 provides an entrance to the internal chambers. When tip 108 is placed in a fluid sample, tip 108 is opened, such as by having its end snapped off when pressure is applied by the user, and the fluid sample is drawn into the first internal chamber and through a filter to fill the vacuum. Target particles are captured by filters inside HHC 100. Elution cartridge 120 stores an elution fluid with a compressed gas. When elution cartridge 120 is manipulated, a valve of elution cartridge 120 is opened, releasing the elution fluid and compressed gas. The elution fluid turns to foam and removes the target particles from the filters. This may be due to a chemical reaction, due to the compressed gas dissolved in the elution fluid expanding due to the change of pressure, etc. The foam then breaks down, leaving the target particles in a small volume of fluid.

FIG. 1B shows a side view of HHC 100, according to an exemplary embodiment of the present invention. This view shows elution cartridge 120 in line with tip 108. Thus, elution cartridge 120 releases the elution fluid which collects the target particles from the filter as the elution fluid moves towards tip 108. Line A-A shows the cut through HHC 100 which produces the view in FIG. 1C.

FIG. 1C shows a cross-sectional view of HHC 100. HHC 100 includes a first internal chamber 110 and a second internal chamber 112. Prior to operation, a vacuum is created in both first internal chamber 110 and second internal chamber 112 using evacuation port 106. First internal chamber 110 is connected to and in fluid communication with tip 108 as well as with elution cartridge 120. Tip 108 may be a breakaway tip, that, when broken, releases the vacuum to begin drawing a fluid sample. A breakaway tip further indicates to a user whether or not HHC 100 has been previously used. To allow tip 108 to break, tip 108 may have a perforation, constructed with a radius of a thinner material, or any other feature enabling it to be broken at a designated place with a mild amount of downward pressure applied by a user.

Within first internal chamber 110 is a filter, such as a hollow fiber filter 114. Hollow fiber filter 114 may be one or more hollow fiber filters. Hollow fiber filter 114 is potted, or glued, into first internal chamber 110 with the bottom of hollow fiber filter 114 located at tip 108 such that when the fluid sample is drawn the fluid sample enters hollow fiber filter 114. For instance, the fluid sample enters the bore of hollow fiber filter 114. In this embodiment, the bore of hollow fiber filter 114 forms a retentate portion of first internal chamber 110, while outside of hollow fiber filter 114 is a permeate portion of first internal chamber 110. Hollow fiber filter 114 includes pores which are sized to the particular particles being captured, i.e. the target particles. Particles smaller than the target particles pass through hollow fiber filter 114 while the target particles are captured. When tip 108 is opened or broken off, the vacuum causes HHC 100 to draw the fluid sample through hollow fiber filter 114. The target particles are captured in hollow fiber filter 114 while fluid from the fluid sample and particles smaller than the filter size are drawn through into the permeate side of first internal chamber 110. When first internal chamber 110 is filled with fluid, tip 108 is withdrawn from the fluid sample to stop drawing the fluid sample.

First internal chamber 110 connects to second internal chamber 112 near the top of each through a fluid channel 111. Fluid channel 111 allows both first internal chamber 110 and second internal chamber 112 to maintain the same vacuum. Second internal chamber 112 is in fluid communication with evacuation port 106. Evacuation port 106 allows for the creation of the vacuum in the chambers 110 and 112, with a valve from which to evacuate air and seal second internal chamber 112. Evacuation port 106 may also allow for the release of the vacuum. Thus, when eluting the target particles, the elution fluid is not drawn through hollow fiber filter 114 by the vacuum. Hollow fiber filter 114 as well as surface tension may prevent fluid drawn through hollow fiber filter 114 from re-entering the bore.

After the fluid sample is drawn, the particles captured by hollow fiber filter 114 may be removed using elution cartridge 120. Elution cartridge 120 includes an elution reservoir 124 containing an elution fluid. The elution fluid may be a water-based solution, such as a surfactant water solution pressurized with a gas such as carbon dioxide. A surfactant may be used in the solution to generate a thicker and dryer foam. Elution cartridge 120 includes a valve 122 that releases the elution fluid when opened. For instance, elution cartridge 120 may release the elution fluid when screwed on to HHC 100. When elution cartridge 120 is connected to the top of HHC 100, elution cartridge 120 is twisted to break a seal on valve 122. The elution fluid travels from the high pressure of elution reservoir 124 to the relatively lower pressure of hollow fiber filter 114 in first internal chamber 110. When the elution fluid is released, the gas releases from the elution fluid in the form of bubbles, creating a foam. The foam travels through hollow fiber filter 114 and recovers the target particles by tangentially flushing the target particles from hollow fiber filter 114. When the foam has exited tip 108, it quickly collapses back to a liquid, leaving a final concentrated product of a much reduced volume of liquid. This volume can be in a range of less than 5 micro liters to 1 milliliter.

Exemplary hollow fiber filters are described in U.S. application Ser. No. 12/882,188, entitled Liquid to Liquid Biological Particle Concentrator with Disposable Fluid Path, filed Sep. 14, 2010, the contents of which are hereby incorporated by reference in their entirety. Hollow fiber filters and other membrane type filters are generally divided into three groups: microfiltration, ultrafiltration, and nanofiltration. Each of these groups is useful for different types of agents being removed from a sample. Nanofiltration filters are not of significant importance here and will not be discussed. Microfiltration refers to those filters with pore sizes of 0.1 micrometer or greater. Ultrafiltration refers to those filters with pore sizes of less than 0.1 micrometer and those in which the pore sizes are generally specified by molecular weight cutoff. Membrane type filters generally may additionally be categorized into hydrophilic and hydrophobic filters. In general hydrophobic pore sizes of less than about 0.65 micrometer will not allow aqueous samples to pass through, unless a wetting agent or solvent is used. Hydrophilic filters will readily pass water, but smaller pore sizes, once wet, will not readily allow air to pass until dried again.

Hollow fiber filters made of different materials are used for application specific reasons. Such fibers are commonly made of mixed cellulose esters (ME), polyethersufone (PES), polysulfone (PS), polypropylene (PP) polyacrylonitrile (PAN), hydrophilic polydivinylidene fluoride (PVDF), and other materials such as stainless steel and ceramics. Various advantages and disadvantages accrue to each type of filter. Some design criteria are the size of pores, biocompatibility, smoothness, fouling potential, and physical strength. Embodiments of hollow fiber filters only allow for the passage of a fluid, but not air, such that after the tip is withdrawn from the fluid sample the HHC locks up.

Alternatively to hollow fiber membrane filters, flat membrane filters of various types may be used. Flat membrane filters are configured such that the internal chamber of the hand-held concentrator is divided into a retentate portion and a permeate portion with the flat filter between the portions. The device is then operated in the same way as hollow fiber filter based hand-held concentrator. Flat membrane filters are commonly made of the same materials and manufacturing practices as hollow fiber membrane filters and have similar characteristics, but often have high pore densities and lower pore size distribution, and thus provide superior performance for some applications. In addition to those flat membrane filters made with the same manufacturing practices as hollow fiber membrane filters, some other flat membrane filters are of significant performance here. Track-etched flat membrane filters have extremely tight pore size distribution and work very well for concentration of particles from samples containing large numbers of interfering particles.

Alternatively to only a tangential sweep, when the entire sample volume has passed through the tip, a backflush of liquid may be used with a secondary tangential sweep with liquid, foam, or a gas. For a number of reasons the use of wet foam is preferred. Two primary reasons for the preference of foam for elution are (1) that a small volume of liquid may be used to create a large volume of foam, thus allowing for smaller elution volumes, and (2) the created foam is much more viscous than the starting surfactant solution, thus allowing for improved passage of the foam through multiple fiber filters.

In addition to surfactant foams that are generated by mixing air and a surfactant solution, the foam may also be generated with a carbonated surfactant solution. Following carbonation under a carbon dioxide head pressure generally in the range of 40 to 300 psi, the fluid is released to a lower pressure zone whereby carbon dioxide is rapidly liberated from the solution, creating small bubbles in the fluid and thereby creating a wet foam. The surfactant foam extraction methods described here can also be used for extraction and cleaning of other collection surfaces in aerosol samplers and collectors. The use of foam to extract these surfaces can provide a significant increase in extraction efficiency and significant decrease in final sample volume. In a preferred embodiment the foam is produced by holding a buffered surfactant solution under a head pressure of carbon dioxide in the elution cartridge and then releasing a volume by opening a timed valve. By controlling both the carbon dioxide pressure and the time that the valve is open the volume of liquid dispensed can be tightly controlled.

Surfactants and foaming agents that may be used in the elution fluid include, but are not limited to Tween 20, Tween 80, Triton X-100, Laureth-12, SDS, and a number of other surfactants and proteins. Certain other materials or chemicals beneficial to downstream sample preparation may be added. These materials may include glass beads used for downstream bead beating for cell lysis, immunomagnetic or magnetic silica beads used for capturing analytes through immunomagnetic type separation, probes and primers for PCR analysis, etc.

In alternative embodiments of the present invention, the vacuum may be created by using a syringe or pump to draw all of the air out of the first internal chamber and second internal chamber. The chambers of the HHC may be of any size. For instance, the first internal chamber may be 5 milliliters in order to draw a fluid sample of this volume. The combined volume of the internal chamber or chambers may be greater than the volume of the fluid sample being drawn such that the vacuum is great enough to draw the entire fluid sample. In other embodiments, the tip may include any means to release the vacuum contained in the chambers. For instance, the tip may include a valve that opens when pushed, a valve that opens when twisted or pulled, a cap over the opening which may be removed to open the vacuum, etc. In related embodiments, the HHC may utilize a flat filter potted perpendicular to the length of the first internal chamber or the single internal chamber of later embodiments. The flat filter may be a depth filter, electret filter, microsieve, charged filter, membrane, zeta potential filter, porous media or other porous surface. The fluid sample is drawn through the flat filter, leaving the target particles on the bottom of the flat filter. The particles can be eluted by backflushing the elution fluid through the filter.

In alternative embodiments, the fluid channel contains a membrane separating the internal chambers. When the fluid sample reaches this membrane, the fluid sample is blocked. Thus, only a volume up to the volume of the first internal chamber may be drawn. In alternative embodiments of the present invention, the tip may be sterilized prior to use. This is accomplished, for instance, by using a sterilizing wipe. Sterilization may be particularly useful in embodiments of the invention not using the breakaway tip, as these embodiments may be used more than one time.

FIG. 2A shows a hand-held concentrator (HHC) 200 utilizing a single internal chamber 218, according to an exemplary embodiment of the present invention. In this embodiment, rather than using a second permeate reservoir to create a larger vacuum, a body 205 surrounds single internal chamber 218. Body 205 may be composed of any rigid or semi-rigid material. Body 205 is preferably transparent such that a user can see the volume of a fluid sample that has been collected. Single internal chamber 218 may be sized such that it is larger than the fluid sample being collected. This sizing is such that when a vacuum is created in single internal chamber 218, the vacuum is able to draw the entire desired volume of the fluid sample. HHC 200 further includes a filter, such as hollow fiber filter 214, an elution cartridge 220, a tip 208, and an evacuation port 207. Hollow fiber filter 214 is similar to the exemplary embodiment disclosed in FIGS. 1A-C, with hollow fiber filter 214 extending from tip 208 to the valve of elution cartridge 220. Elution cartridge 220 and tip 208 are similar to the embodiment of FIGS. 1A-C. Evacuation port 207 is located on a side of body 205 of HHC 200. Evacuation port 207 is used to create the vacuum inside single internal chamber 218. Evacuation port 207 may also be used to release the vacuum from single internal chamber 218, for instance, when eluting particles from hollow fiber filter 214. HHC 200 may include one or more graduations 219. Graduations 219 may be used to determine when an appropriate volume of the fluid sample has been collected.

FIG. 2B shows a side view of HHC 200, according to an exemplary embodiment of the present invention. In this embodiment, elution cartridge 220 is aligned with tip 208. Line A-A shows the cut through HHC 200 which produces the view shown in FIG. 2C.

FIG. 2C shows a cross-sectional view of HHC 200, according to an exemplary embodiment of the present invention. In this embodiment, HHC 200 includes elution cartridge 220 including an elution valve 222 and elution reservoir 224, evacuation port 207, single internal chamber 218, tip 208, and a filter, such as hollow fiber filter 214.

With a vacuum created in single internal chamber 218 using evacuation port 207; tip 208 is placed in a fluid sample. Tip 208 is removed or opened, opening the vacuum and drawing the fluid sample through a retentate portion of single internal chamber 218, through hollow fiber filter 214, and into a permeate portion of single internal chamber 218, capturing target particles on the bore of hollow fiber filter 214. Unwanted liquids/solutions and other particulates pass through hollow fiber filter 214 into the permeate portion of single internal chamber 218. When an appropriate volume of the fluid sample has been collected, HHC 200 is lifted, thereby removing tip 208 from the fluid sample. Elution cartridge 220 is then manipulated by the user to open elution valve 222 and release the elution fluid and gas combination from elution reservoir 224. The elution fluid becomes a foam and elutes the target particles from hollow fiber filter 214 and out of tip 208, where the target particles may be collected.

The evacuation port may further be used to release any remaining vacuum after the desired amount of fluid has been sampled. This helps to prevent any of the elution fluid from being pulled into the permeate side of the hollow fiber filter during elution, or to remove the fluid prior to elution of a flat filter.

FIG. 3A shows an elution cartridge 320, according to an exemplary embodiment of the present invention. Elution cartridge 320 is generally a small pressurized reservoir containing an elution fluid, such as a surfactant water solution, pressurized by a gas, such as carbon dioxide. In this embodiment, elution cartridge 320 includes a body 321, a valve 322, a reservoir 324, and a connector 328. Body 321 is composed of a rigid or semi-rigid material. For instance, body 321 may be made of a metal, plastic, composite, etc. Connector 328 allows elution cartridge 320 to couple to a hand-held concentrator, to an elution assembly such as that in FIGS. 8A and 8B, etc. Valve 322 ensures the contents of elution cartridge 320 remain inside reservoir 324 until valve 322 is manipulated. Valve 322 may be, for instance, a screw on valve which releases the contents when screwed in. Valve 322 may alternatively open at the press of a button, when a seal is broken, when pressed in, etc.

Figure 3A:
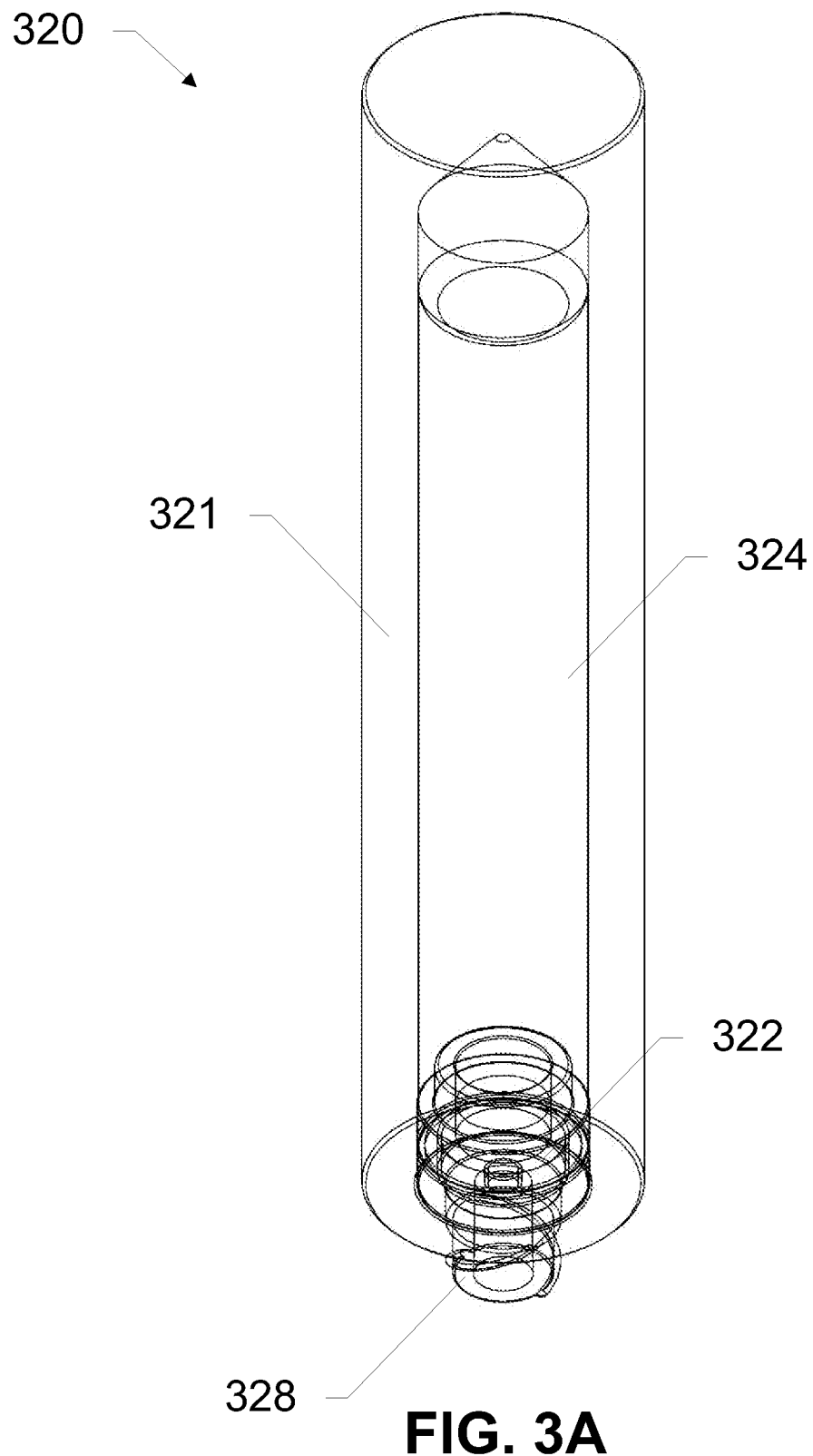
FIGS. 3A-C show an elution cartridge, according to an exemplary embodiment of the present invention.
Figure 3B:
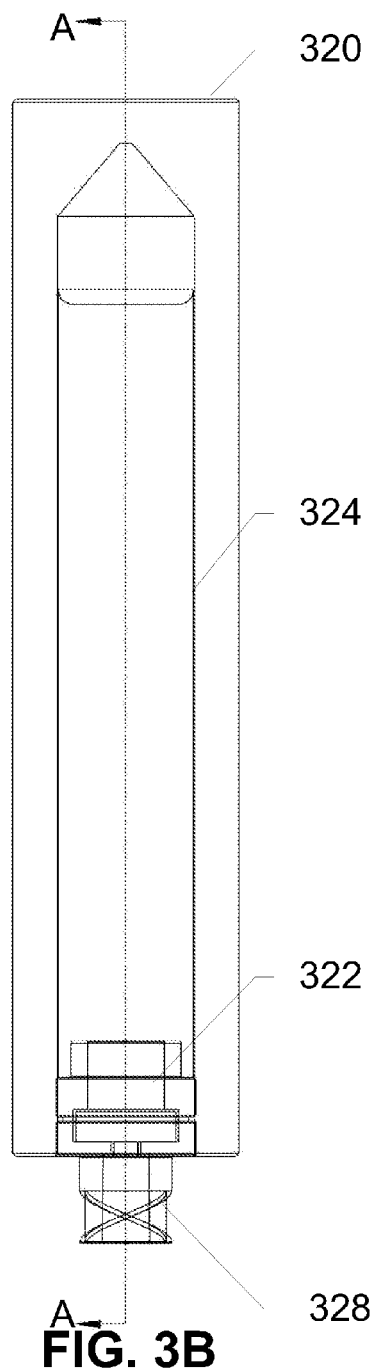

FIG. 3B shows a side view of elution cartridge 320, according to an exemplary embodiment of the present invention. In this embodiment, elution cartridge 320 includes an elution reservoir 324, valve 322, and connector 328. Line A-A shows the cut through elution cartridge 320 which produces the view shown in FIG. 3C.

Figure 3C:
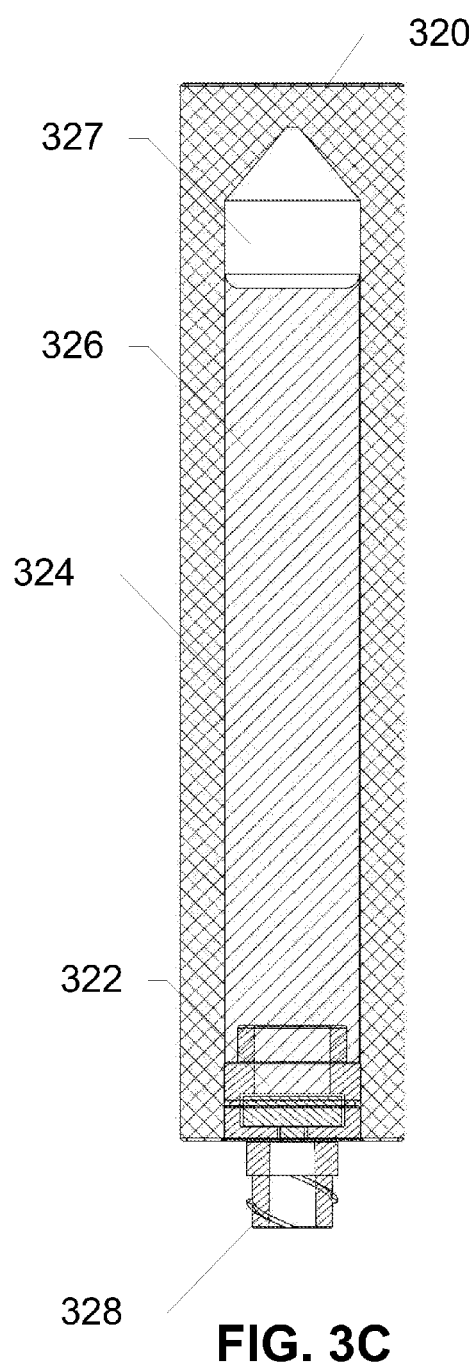
Figure 4:
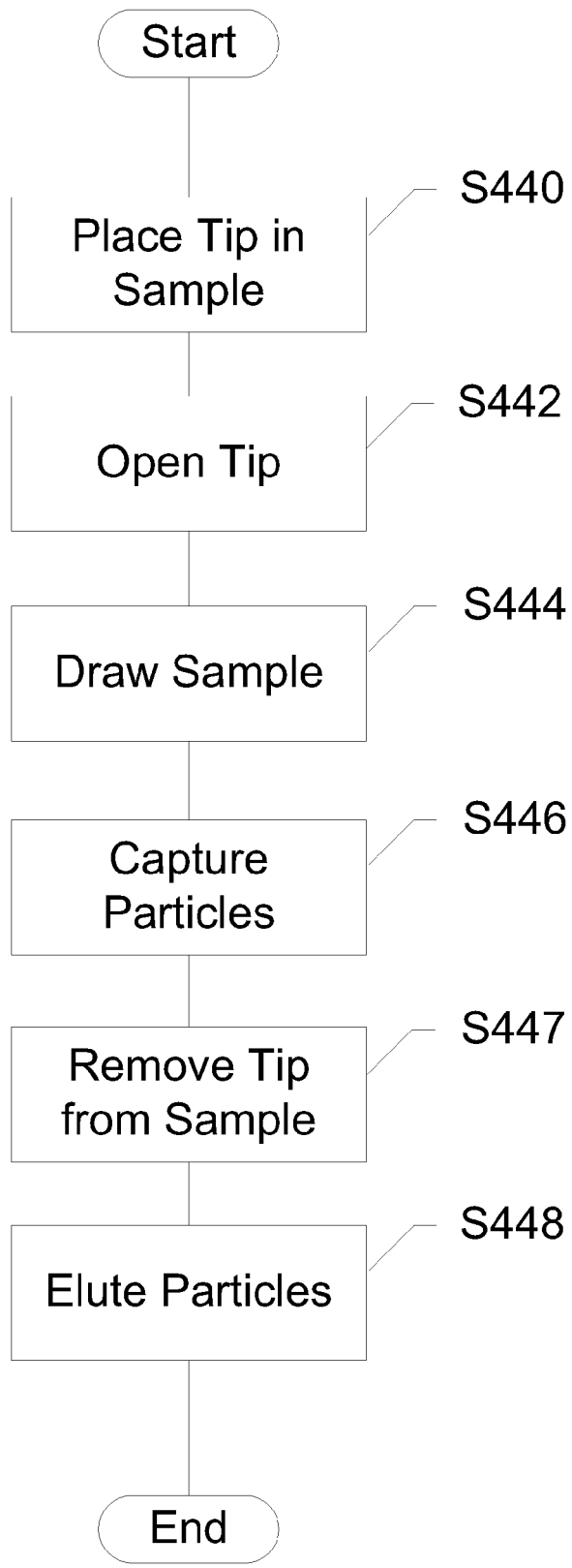
FIG. 4 shows a method of collecting particles from a fluid sample, according to an exemplary embodiment of the present invention.
Figure 5A:
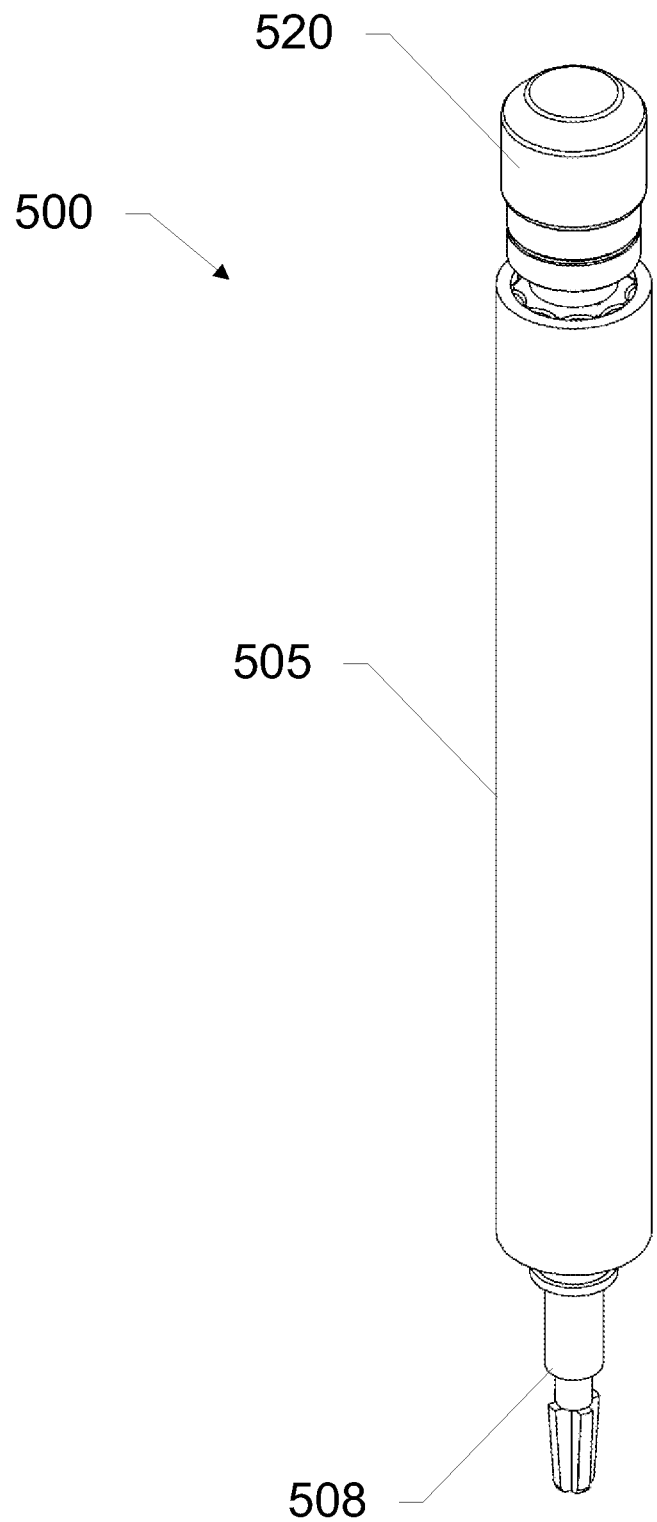
FIGS. 5A-C show a hand-held concentrator (HHC) utilizing absorption, according to an exemplary embodiment of the present invention.
Figure 5B:
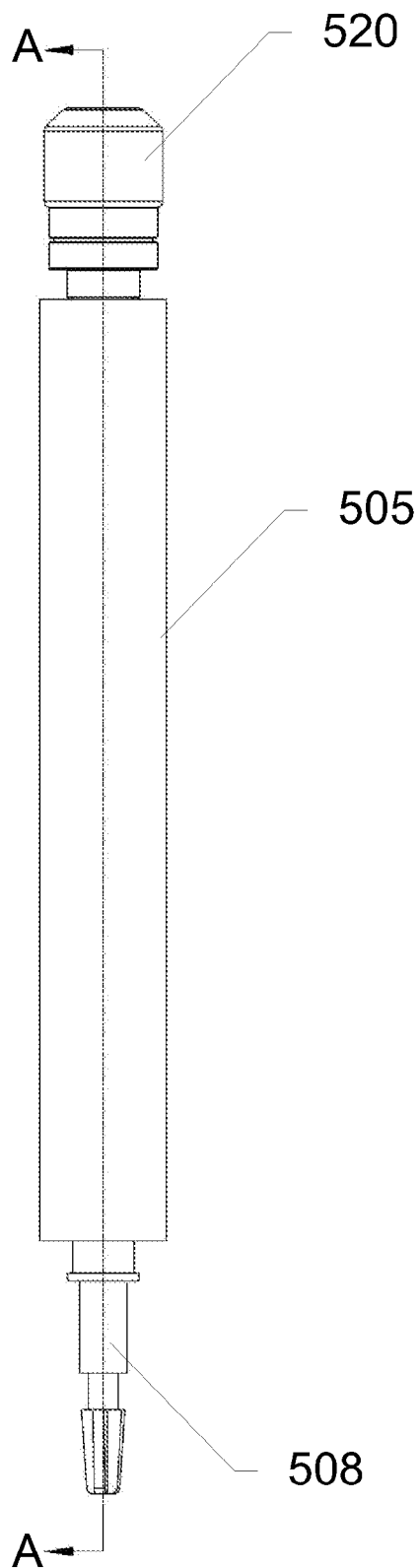
Figure 5C:
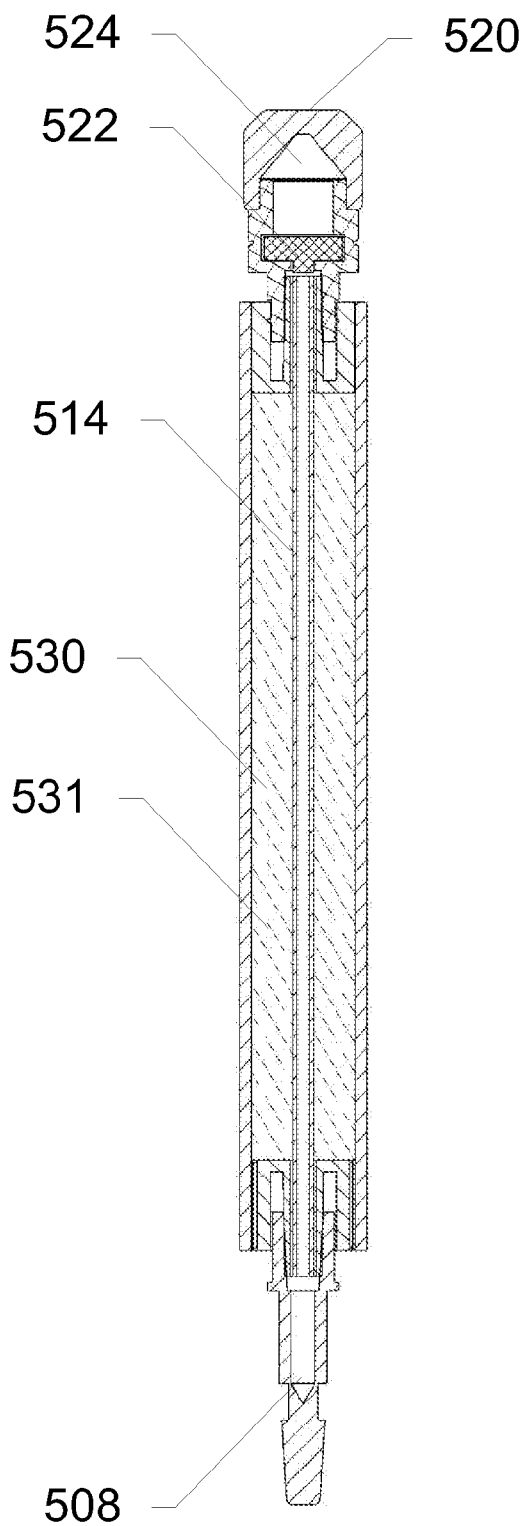

FIG. 3C shows a cross-sectional view of elution cartridge 320, according to an exemplary embodiment of the present invention. This view shows elution reservoir 324 containing an elution fluid 326 and a compressed gas 327. Elution fluid 326 may be a surfactant water solution. Compressed gas 327 is a gas, such as carbon dioxide, which in addition to maintaining pressure inside elution reservoir 324, is dissolved into elution fluid 326 when under pressure. When valve 322 of elution cartridge 320 is opened, elution fluid 326 exits elution reservoir 324 via connector 328, going from the high pressure environment of elution reservoir 324 to the relatively lower pressure environment outside of elution cartridge 320. This pressure change causes the dissolved compressed gas 327 to expand into micro bubbles in elution fluid 326, which creates foam. Additionally, compressed gas 327 expands to force all of elution fluid 326 out of elution reservoir 324. Thus, when used in combination with a hand-held concentrator coupled to elution cartridge 320, the foam exits connector 328 and into the hand-held concentrator where it elutes target particles from a filter of hand-held concentrator.

To further improve efficiency, a biocompatible surfactant such as Tween 20 or Triton X-100 may be added to the elution cartridge at low levels, such as 0.01% to 0.2% by volume. This liquid is an insignificant volumetric addition, but can increase throughput efficiency from the 40% to 65% range to nearly 100%. Buffered surfactant solutions such as 25 mM tris buffered saline (TBS) or phosphate buffered saline (PBS) with 0.01% to 0.2% Triton X-100 or Tween 20 are commonly used in the collection fluids of bioaerosol samplers.

FIG. 4 shows a method of collecting particles from a fluid sample, according to an exemplary embodiment of the present invention. In this embodiment, a hand-held concentrator (HHC) is provided with a means for drawing a fluid sample, such as by utilizing one or more vacuum chambers. A tip of the HHC is placed into the fluid sample S440. The tip of the HHC is then opened S442. The tip may be opened by applying downward pressure to break off the tip, by opening a valve on the tip, uncapping the tip, etc. With the tip opened, the HHC draws the fluid sample into the HHC and through a filter S444. The drawing may occur due to a vacuum in the chamber or chambers of the HHC, due to a wicking or absorbent material in a chamber of the HHC, etc. The filter may be, for instance, a hollow fiber filter, a flat filter, etc. As the fluid sample is being drawn through the filter, target particles are captured on the filter S446. When an appropriate amount of the fluid sample has been drawn, the tip of the HHC is removed from the fluid sample S447. The tip may then be positioned above a sample cup and the particles eluted S448. This may occur by releasing a surfactant solution from an elution cartridge, creating foam that sweeps through the filter, elutes the particles from the filter, and transports the particles out via the tip.

FIG. 5A shows a hand-held concentrator (HHC) 500 utilizing absorption, according to an exemplary embodiment of the present invention. Rather than including a vacuum chamber, HHC 500 utilizes an absorbent material to draw a fluid sample into HHC 500. In this embodiment, HHC 500 includes an elution cartridge 520, a body 505, and a tip 508. Each of elution cartridge 520, body 505, and tip 508 are similar to those of other embodiments, particularly those of FIGS. 2A-C.

FIG. 5B shows a side view of HHC 500, according to an exemplary embodiment of the present invention. Elution cartridge 520 is thus preferably aligned with tip 508. Line A-A shows the cut through HHC 500 which produces the view shown in FIG. 5C.

FIG. 5C shows a cross-sectional view of HHC 500, according to an exemplary embodiment of the present invention. In this embodiment, HHC 500 includes elution cartridge 520 including an elution valve 522 and elution reservoir 524, single internal chamber 531, tip 508, and a filter, such as hollow fiber filter 514. HHC 500 further includes an absorbent material 530 to draw the fluid sample into HHC 500. Absorbent material 530 may be, for instance, an absorbent gelling material (AGM). An AGM is a cross-linked polyacrylate, about 75% neutralized with Na+ (sodium) ions, in the form of a white granular powder. An AGM can generally absorb about thirty times its own weight in aqueous liquids. An AGM may include superabsorbers, supersorbers, superabsorbent polymers (SAP), superabsorbent material (SAM), hydrogels, hydrogel-forming polymers, etc. Cellulose can absorb about four times its weight, and is often mixed with AGM.

To use HHC 500, tip 508 is placed in a fluid sample. Tip 508 is manipulated, allowing absorptive material 530 to draw the fluid sample through a retentate portion of single internal chamber 531, through hollow fiber filter 514, and into a permeate portion of single internal chamber 531, capturing target particles on hollow fiber filter 514. Unwanted liquids/solutions and other particulates pass through hollow fiber filter 214 and are absorbed by absorbent material 530. When an appropriate volume of the fluid sample has been collected, tip 508 is removed from the fluid sample. Elution cartridge 520 is then manipulated, opening elution valve 522 and releasing the elution fluid and gas combination from within elution reservoir 524. The surfactant solution becomes foam and elutes the target particles from hollow fiber filter 514 and out of tip 508, where the target particles may be collected.

FIG. 6A shows an HHC 600 including a syringe 632, according to an exemplary embodiment of the present invention. In this embodiment, HHC 600 includes a body 602 similar to that of the embodiment in FIGS. 1A-C. Similarly, body 602 encloses internal chambers. HHC 600 includes syringe 632, syringe 632 having a mechanical syringe plunger that inserts into one of the internal chambers and is pulled out to create a vacuum. Syringe 632 includes a locking tab 633 so that syringe 632 may be locked when the vacuum has been created in order to maintain the vacuum.

FIG. 6B shows a side view of HHC 600, according to an exemplary embodiment of the present invention. Line A-A shows the cut through HHC 600 which produces the view shown in FIG. 6C.

FIG. 6C shows a cross-sectional view of HHC 600, according to an exemplary embodiment of the present invention. In this embodiment, HHC 600 includes syringe 632, locking tab 633, a first internal chamber 610, a second internal chamber 612, a fluid channel 611, elution cartridge 620 including an elution valve 622 and an elution reservoir 624, a hollow fiber filter 614, and tip 608. The components of HHC 600 with a corresponding component in HHC 100 include generally the same features as these counterparts. As stated above, syringe 632 is pulled out of second internal chamber 612 to create a vacuum in second internal chamber 612 and therefore in first internal chamber 610. At this point, HHC 600 operates in an equivalent manner to HHC 100 in FIGS. 1A-C. Briefly, when using HHC 600, a user first pulls the syringe out from body 602 to create a vacuum. With the vacuum created, HHC 600 may be used in a similar manner to the embodiment of FIGS. 1A-C. Tip 608 is placed in a fluid sample and manipulated to open the vacuum. The fluid sample is drawn into tip 608, through a retentate portion of first internal chamber 610, and through hollow fiber filter 614 into a permeate portion of first internal chamber 610. Target particles are captured in the bore, or retentate side, of hollow fiber filter 614, while unwanted liquids/solutions and other particulates pass through hollow fiber filter 614 and enter the permeate portion of first internal chamber 610. The target particles may then be eluted by manipulating elution cartridge 620, opening elution valve 622 and releasing the elution fluid into hollow fiber filter 614 and through tip 608.

HHC 600 may also be used without first creating a vacuum in first internal chamber 610 and second internal chamber 612. A user may place tip 608 in the fluid sample, open tip 608, and use syringe 632 to draw the fluid sample into HHC 600. The user pulls syringe 632 out from second internal chamber 612, drawing the fluid sample into tip 608, through the retentate portion, through hollow fiber filter 614, and into the permeate portion of first internal chamber 610. The target particles are captured on the retentate side of hollow fiber filter 614. When an appropriate volume of the fluid sample has been drawn, the user ceases to pull up on syringe 632. The user may then manipulate elution cartridge 620 to elute the target particles from hollow fiber filter 614.

Figure 2A:
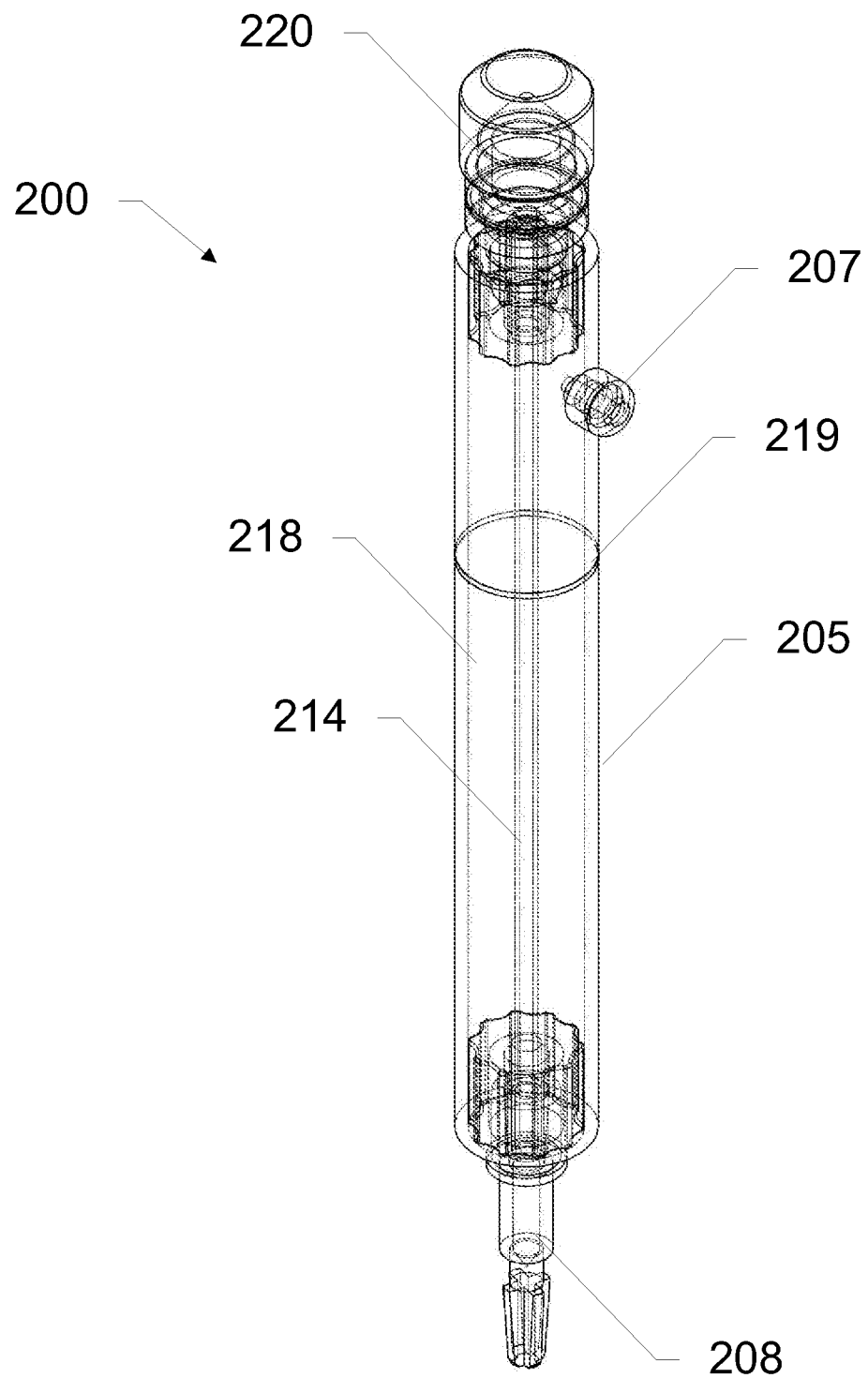
Figure 6A:
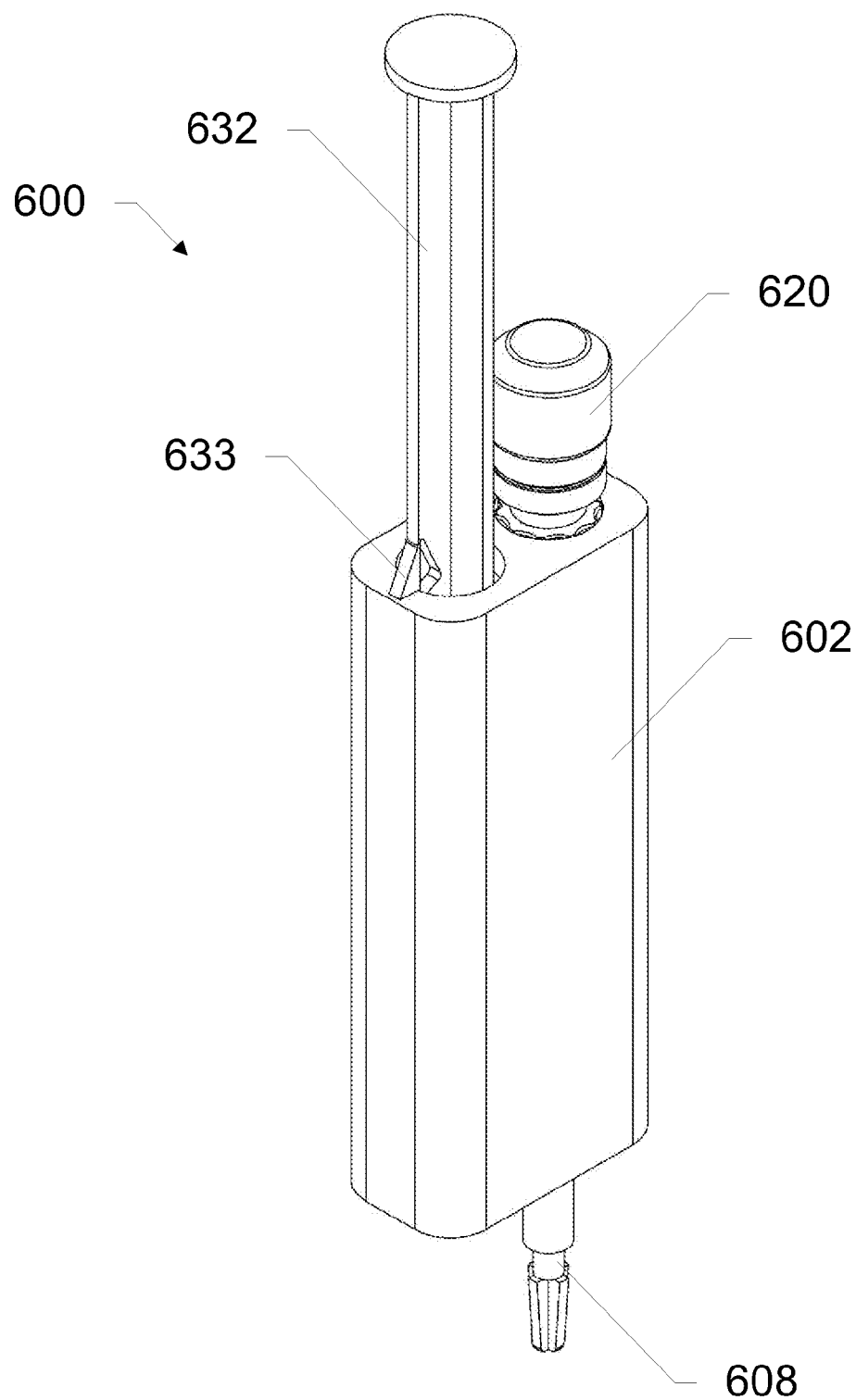
Figure 7A:
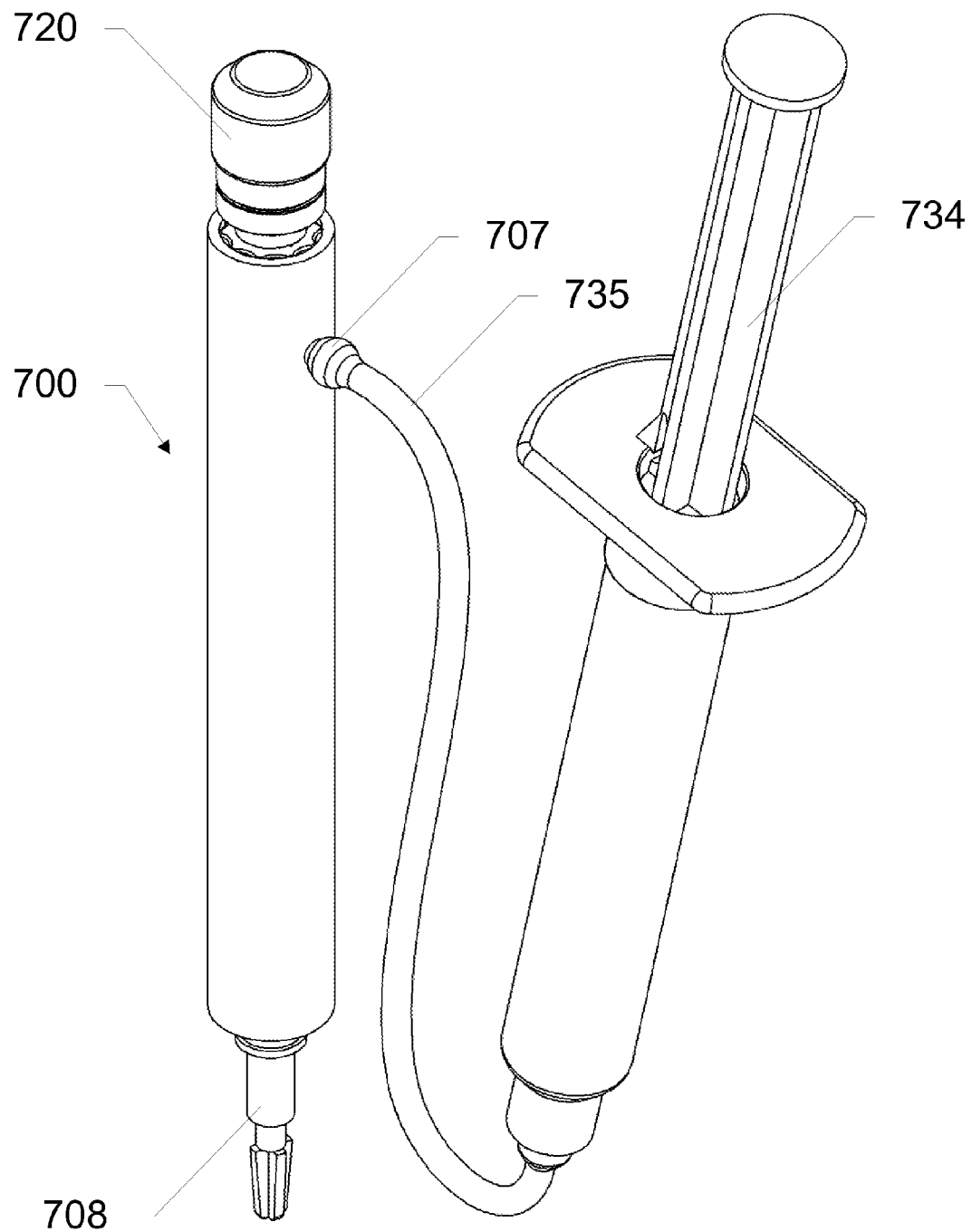
FIGS. 7A-C show a hand-held concentrator with an external syringe, according to an exemplary embodiment of the present invention.

FIG. 7A shows a hand-held concentrator 700 with an external syringe 734, according to an exemplary embodiment of the present invention. In this embodiment, HHC 700 has a single internal chamber, similar to that of FIGS. 2A-C. HHC 700 includes a side port 707, an elution cartridge 720, and a tip 708. Side port 707 connects to external syringe 734 through a connecting tube 735. Connecting tube 735 is generally a flexible tube, such as polyurethane, PVC, polyethylene, etc., which couples to the end of external syringe 734 and to side port 707. External syringe 734 is used to create a vacuum in the single internal chamber of HHC 700. HHC 700 with external syringe 734 operates similarly to HHC 600, shown in FIGS. 6A-C, but with the syringe being external, or removably coupled to HHC 700.

Figures 7B, 7C:
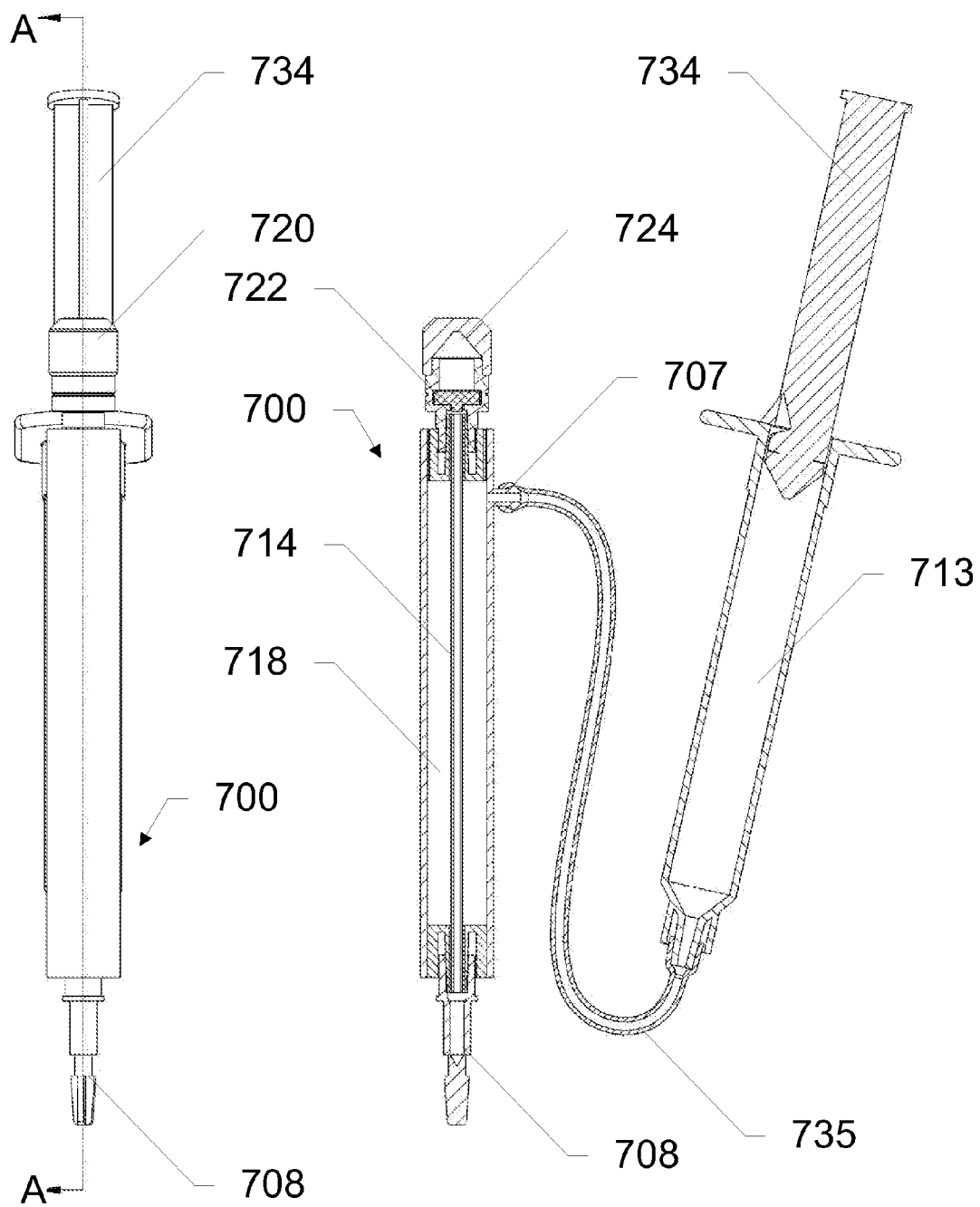

FIG. 7B shows a side view of HHC 700 and external syringe 734, according to an exemplary embodiment of the present invention. Line A-A shows the cut through HHC 700 and external syringe 734 which produces the view shown in FIG. 7C.

FIG. 7C shows a cross-sectional view of HHC 700 and external syringe 734, according to an exemplary embodiment of the present invention. External syringe 734 includes an external chamber 713. External syringe 734 connects to HHC 700 through connecting tube 735. HHC 700 includes elution cartridge 720 which encompasses an elution valve 722 and an elution reservoir 724, a hollow fiber filter 714, a single internal chamber 718, side port 707, and tip 708.

External chamber 713 expands when the plunger of syringe 734 is pulled out of external chamber 713, creating a vacuum in external chamber 713 and single internal chamber 718. This vacuum is used to draw a fluid sample into tip 708, through a retentate portion of single internal chamber 718, and through hollow fiber filter 714 after tip 708 has been opened, capturing target particles. Unwanted liquids/solutions and other particulates pass through hollow fiber filter 214 into a permeate portion of single internal chamber 718. When enough of the fluid sample has been drawn, tip 708 is removed from the fluid sample. Tip 708 is placed above a collection cup, test tube, etc., and elution cartridge 720 is manipulated. This manipulation opens elution valve 722 to release the elution fluid and gas from elution reservoir 724. The elution fluid turns to foam and elutes the target particles from hollow fiber filter 714, transporting them to an external environment via tip 708 for further analysis.

Alternatively, external syringe 734 may be used to draw the fluid sample into tip 708, through the retentate portion, and through hollow fiber filter 714. Also, while a syringe is shown, any mechanical vacuum source could also be used.

Figure 8A:
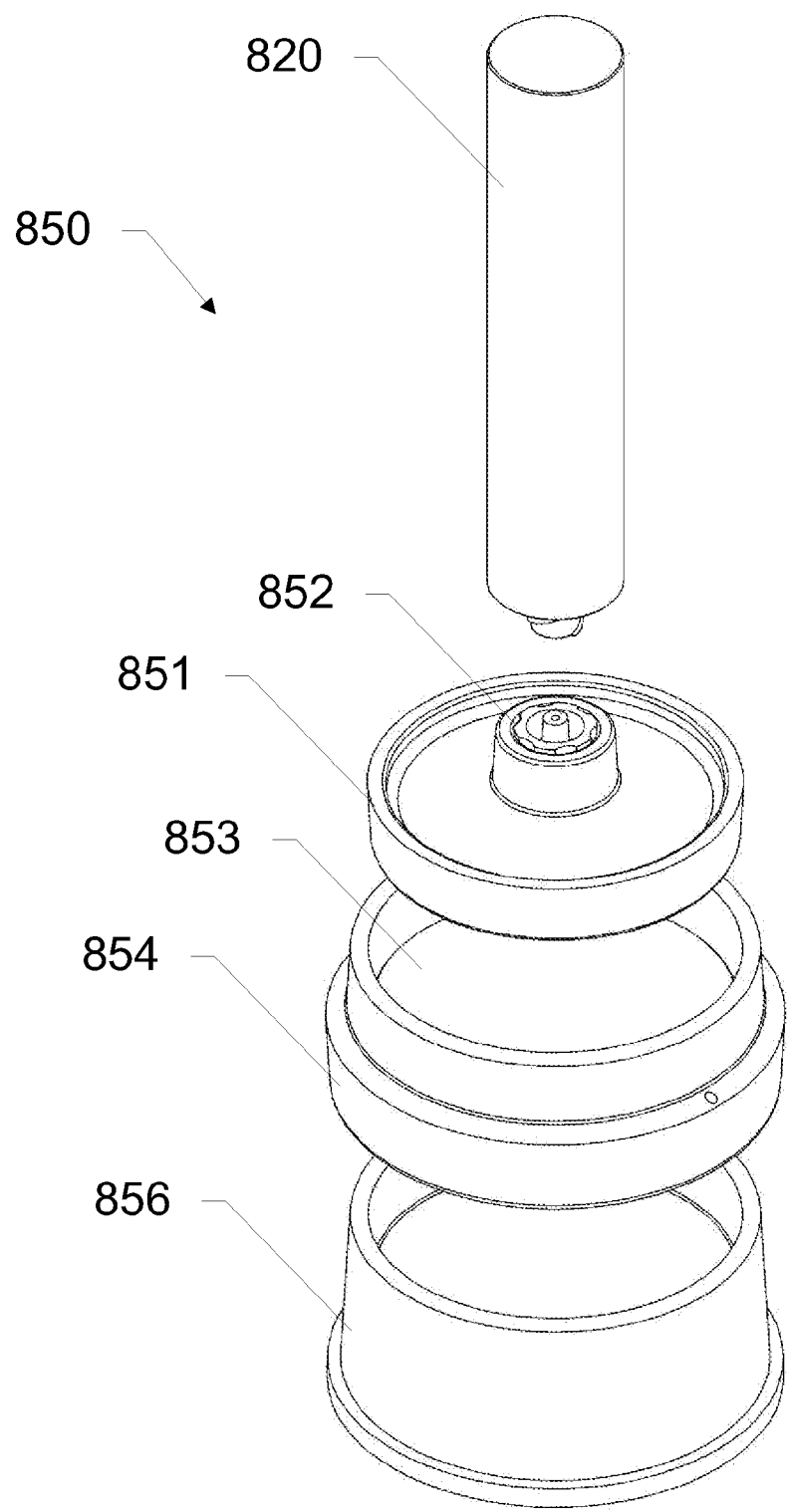
FIGS. 8A-B show a flat, depth filter elution assembly and elution cartridge, according to an exemplary embodiment of the present invention.

FIG. 8A shows a flat, depth filter elution assembly 850 and an elution cartridge 820, according to an exemplary embodiment of the present invention. In this embodiment, elution assembly 850 includes elution cartridge 820, a lid 851, a connector 852, a filter media 853, a filter cassette 854, and a sample container 856. Lid 851, filter cassette 854, and sample container 856 may be composed of any substantially rigid material, such as metal, plastic, etc. Elution cartridge 820 is equivalent to other elution cartridges described previously. Elution cartridge 820 sealingly attaches to connector 852 of lid 851. Lid 851 couples to filter cassette 854, sealing filter media 853 between lid 851 and filter cassette 854. Filter media 853 may be removed from a concentrator device, such as an HHC or an aerosol sampler, and placed in elution assembly 850. Filter media 853 may be aligned with a retentate side of filter media 853 facing up or down, depending upon the desired result. Filter cassette 854 couples to sample container 856 such that any target particles on filter media 853 stay contained within elution assembly 850 during use.

Figure 8B:
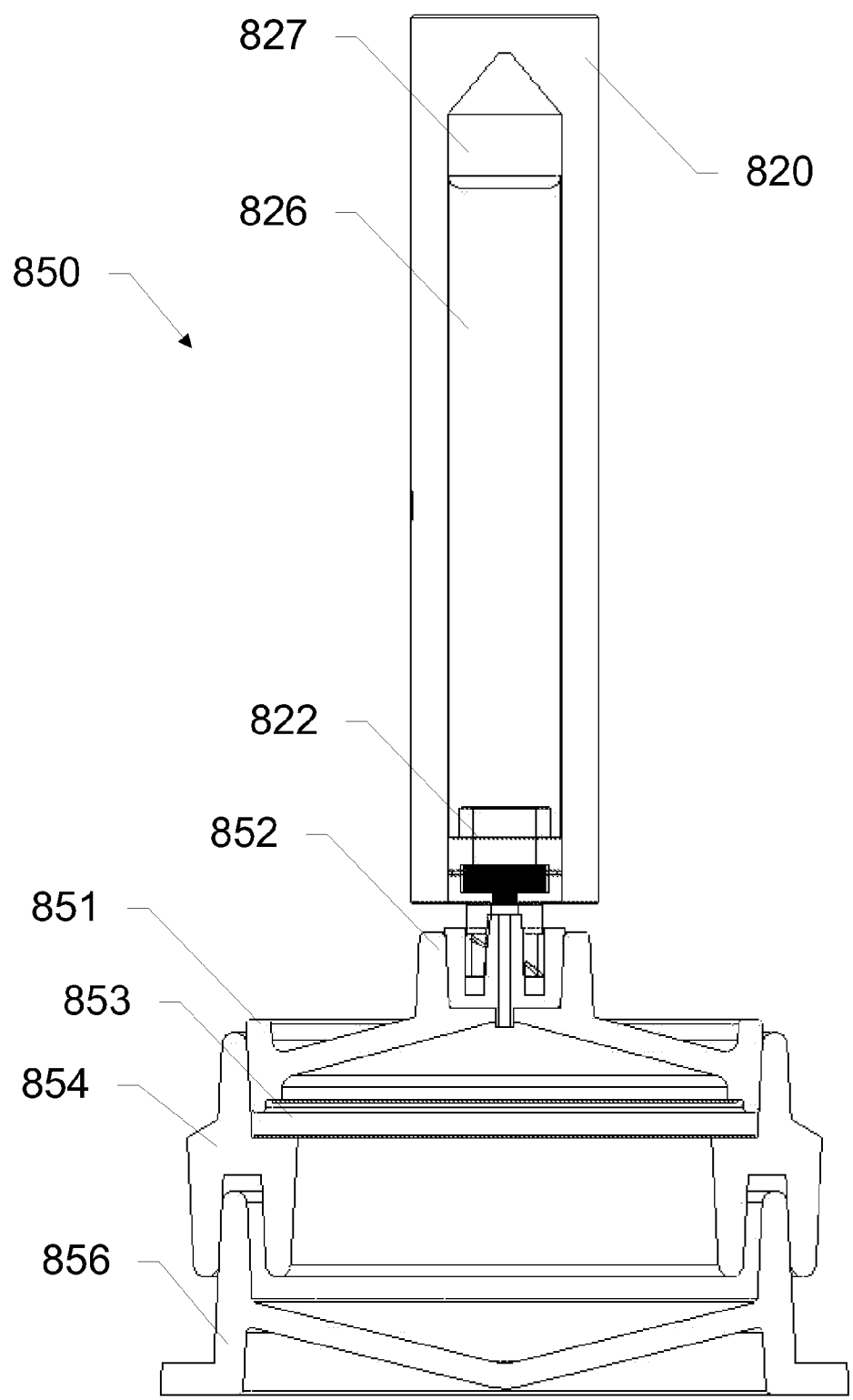

FIG. 8B shows the internal components of elution assembly 850, according to an exemplary embodiment of the present invention. In this embodiment, elution assembly 850 includes elution cartridge 820 containing an elution fluid 826 and a compressed gas 827, an elution valve 822, connector 852, lid 851, filter media 853, filter cassette 854, and sample container 856. Elution valve 822 may combine with connector 852 to create a release mechanism for elution valve 822. For instance, elution valve 822 may be a female luer lock valve with connector 852 including a male luer lock valve, such that the combination allows for release of the contents of elution cartridge 820.

When elution cartridge 820 is manipulated, elution valve 822 is opened and compressed gas 827 pushes the elution fluid through connector 852 as it turns to foam. The foam pushes through filter media 853, removing target particles from the retentate side of filter media 853. The target particles and foam are collected in sample container 856. The foam breaks down, leaving the target particles in a small volume of liquid.

Filters and elution techniques are further described in U.S. application Ser. No. 12/883,137, entitled Devices, Systems and Methods for Elution of Particles from Flat Filters, filed Sep. 15, 2010, the contents of which are hereby incorporated by reference in their entirety. Wet foam has unique properties that make it a superior method for extracting biological material from flat depth filters, such as the electret filters described here, and from hollow fiber membrane filters. Possibly the most important aspect of using wet foam for extraction is the advantage gained by expanding the extraction fluid to many times its original volume. When using fluids for extraction, most of the fluid is used to fill the internal void volume of the interstitial spaces in depth filters or in the bore of hollow fibers, rather than performing the actual extraction at the surface. The elution fluid is expanded to 5 to 20 times the original liquid volume, allowing a large volume of the wet foam to be swept through the filter while keeping the final extraction volume small. Expansion of the elution fluid and increased viscosity lead to contact with each fiber surface in flat depth filters and hollow fiber filters. A reduced boundary layer found in flowing foams allows extraction forces to act at the surface.

Foam has been used and studied extensively for use in semiconductor cleaning, radioactive particle removal, and for decontamination of biological agents. Foams are also frequently used during hydrocarbon exploration with the most common use in the area of enhanced oil recovery. Due to the high viscosity of foams, they exhibit reduced channeling thereby sweeping more oil out of porous media (Yan et al., 2006). This same characteristic makes foam ideal for extraction of flat depth filters and hollow fiber filters. It is well known that channeling or non-uniform flow distribution takes place in hollow fiber modules that contain multiple fibers (Park and Chang, 1986; Pangrle et al., 1989; Ronco et al., 2002). Channeling is dependent on inlet manifold design, Reynolds number, pressure drop, and other issues such as irregularity in fiber diameter (Park and Chang, 1986; Pangrle et al., 1989). In short, channeling is difficult to control and is almost certainly a factor during recovery of organisms from multiple fiber concentration units with aqueous extraction fluids. Flushing a liquid through a flat depth filter also results in channeling, but because of the reduced pressure drop and large void volume the effect is increased. Utilizing the wet foam elution method allows the entire filter to be extracted in a single pass.

The foam moves as a rigid body lubricated by water generated by breaking foam at the wall (Briceno and Joseph, 2003). Because core flow is absent and the lubricating layer is thin, the foam is able to act at the filter surface to sweep away the captured particles. Further, energy created by breaking bubbles may enhance particle removal from the electret fiber or hollow fiber surface. The majority of the bubbles in the carbonated, extraction foam burst soon after release from the concentration cell, returning the foam to a liquid and allowing for transfer to the identifier or other sample preparation steps as an aqueous sample. Most of the foam returns to a liquid state within 30 seconds.

In practice, a PTFE-lined elution cartridge is filled with elution fluid and carbon dioxide is added through a fritted bubbler until a head pressure of 100 to 450 psi is attained. The reservoir of the elution cartridge is then held at constant pressure. The carbon dioxide is now in solution with the elution fluid containing 3 to 20 times its own volume of carbon dioxide at ambient pressure. Controlled volumes of the elution fluid are dispensed with a timer controlled dispensing valve. When the elution fluid is released through the dispensing valve and returns to atmospheric pressure, carbon dioxide comes out of solution as small bubbles, creating wet foam. The wet foam is swept through the interstitial spaces of the flat electret filter to efficiently extract particles. Within seconds after extraction the foam returns to a liquid making it available for sample processing and analysis. If desired, a non-aqueous fluid such as polyethylene glycol can be used as a constituent of the extraction fluid to depress the freezing point of the liquid.

Embodiments of the elution cartridge may use a self-opening female luer lock valve. The valve remains closed until it is connected to a male luer lock valve on an HHC, on a flat, depth filter elution assembly, etc. In other embodiments, the elution cartridge has a manually operated slider valve. The elution cartridge is locked onto the article to be eluted and then the valve is manually opened to dispense the extraction fluid. Further, a diffuser screen may be utilized to uniformly spread the wet foam over the entire filter surface. This is especially important with low pressure drop filter types such as extremely open electret filter types.

A small volume of elution fluid may be used to create a large volume of foam. Since the boundaries of the bubbles present in the foam must remain intact to remain as foam, the boundaries of the bubbles at the interface of the filter and the extraction foam must always be touching. When the foam is extracted from the device and collapses, the remaining product is a small volume of liquid. This volume can be in a range of less than 5 microliters to 1 milliliter.

Figure 9A:
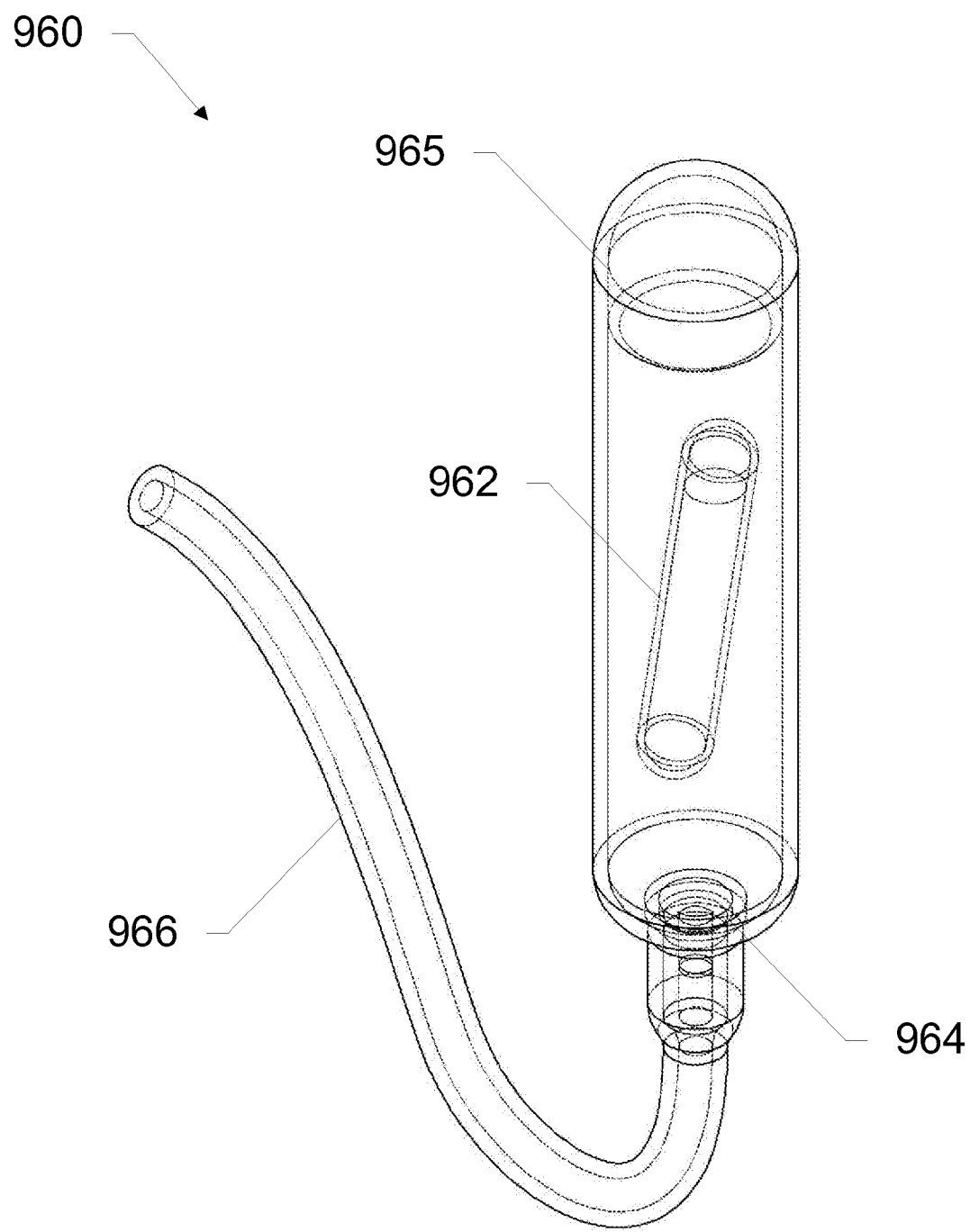

FIG. 9A shows an elution cartridge 960, according to an exemplary embodiment of the present invention. In this embodiment, elution cartridge 960 includes a flexible body 965 surrounding a breakable ampule 962, a burst disk 964, and a connection tube 966. Flexible body 965 may be bent, twisted, compressed, etc. without being permanently deformed, in order to break breakable ampule 962. Breakable ampule 962 is a small chamber containing a reagent. Burst disk 964 initially seals an internal chamber of flexible body 965. When a set amount of pressure is built inside the internal chamber of flexible body 965, burst disk 964 ruptures or breaks, releasing the contents of flexible body 965. The contents travels through connection tube 966 into, for instance, an HHC as described in the above embodiments. Connecting tube 966 is generally a flexible tube, such as polyurethane, PVC, polyethylene, etc., which couples elution cartridge 960 to a device being eluted, such as an HHC.

FIG. 9B shows a side view of elution cartridge 960, according to an exemplary embodiment of the present invention. Line A-A shows the cut through elution cartridge 960 which produces the view shown in FIG. 9C.

FIG. 9C shows a cross-sectional view of elution cartridge 960, according to an exemplary embodiment of the present invention. This view shows the internal components of elution cartridge 960, including breakable ampule 962, a first reagent 961, a second reagent 963 within breakable ampule 962, and burst disk 964. First reagent 961 and second reagent 963 may be any two materials or fluids which react to produce gas, such as carbon dioxide, when in contact with each other. First reagent 961 further includes an elution fluid which is pressurized by the produced gas. Examples of possible reagents include an acid and a metal carbonate. Possible acids include, but are not limited to hydrochloric acid, sulfuric acid, citric acid, tartaric acid, benzoid acid, etc. Possible metal carbonates include, but are not limited to sodium bicarbonate, calcium carbonate, sodium carbonate, potassium carbonate, iron carbonate, calcium-magnesium carbonate, etc. The produced carbon dioxide goes into solution through turbulent mixing that occurs as foaming or bubbling during the reaction and creates head pressure within the closed reaction space of flexible body 965. In addition to the two reagents 961 and 963, buffers, salts, growth media, and other materials may be added to the reaction. Adding a buffer such as tris, phosphate buffer, or phosphate buffered saline may be added to maintain a neutral pH, as carbonic acid formed in the liquid can cause the solution to become more acidic. Flexible body 965 is manipulated such that breakable ampule 962 is broken, allowing first reagent 961 to mix with second reagent 963. This mixing causes a chemical reaction, producing a gas. The gas pressurizes the internal chamber of flexible body 965 until burst disk 964 ruptures, releasing the pressurized fluid through connecting tube 966.

In embodiments of the elution cartridge, the elution cartridge may have a valve rather than a burst disk. This allows for multiple uses of the same elution cartridge. For instance, the valve may be manipulated in order to release a metered dose of the pressurized fluid. This may be performed multiple times using the same elution cartridge. Similar to previous embodiments of an elution cartridge, this valve may open in many ways, such as by twisting the elution cartridge, by pushing in the elution cartridge, by a set amount of pressure, etc.

Figure 10A:
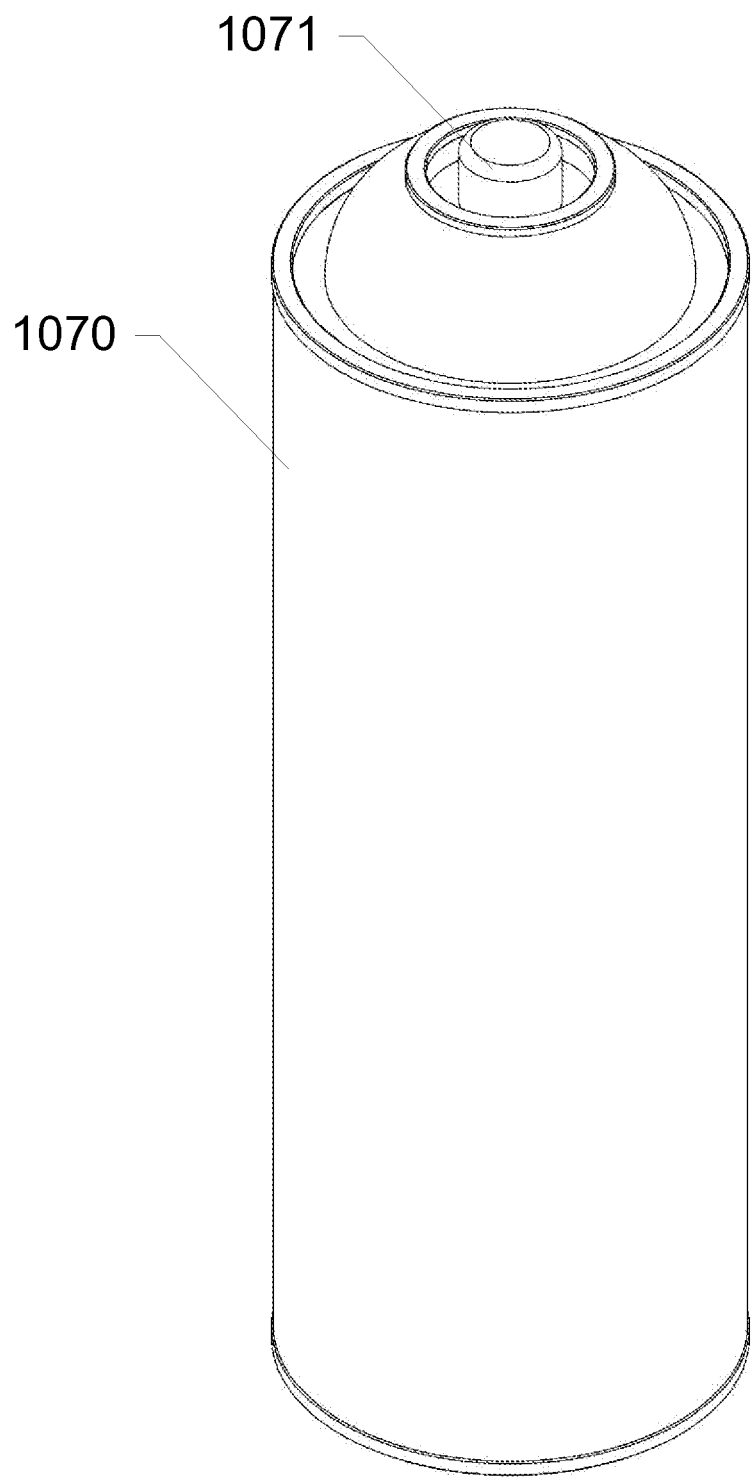

FIG. 10A shows an elution cartridge 1070, according to an exemplary embodiment of the present invention. Elution cartridge 1070 is used to elute particles from a filter of a device. In this embodiment, elution cartridge 1070 is a similar shape to a spray paint can. Elution cartridge 1070 includes a nozzle 1071, or valve. Nozzle 1071 may be formed in many different configurations such that it may be used for different devices. For instance, elution cartridge 1070 may be used with an HHC, with a flat, depth filter elution assembly, etc. Elution cartridge 1070 may be designed for a single use, or for multiple uses. Elution cartridge 1070 may be refilled or replaced after it has been used. Nozzle 1071 may be a puncture disk that screws or is pushed into a piercing fitting on a device. Alternatively, nozzle 1071 may be an on/off valve or a pressure release valve. Nozzle 1071 may further be a valve that releases a metered dose when pushed down onto a fitting. Thus, embodiments of nozzle 1071 allow for multiple extractions using the same elution cartridge 1070.

FIG. 10B shows a side view elution cartridge 1070, according to an exemplary embodiment of the present invention. Line A-A shows the cut through elution cartridge 1070 which produces the view shown in FIG. 10C.

FIG. 10C shows a cross-sectional view of elution cartridge 1070, according to an exemplary embodiment of the present invention. In this embodiment, the interior of elution cartridge 1070 holds an elution fluid 1026 and a compressed gas 1027. With the chamber under high pressure, compressed gas 1027 may dissolve into elution fluid 1026. As long as elution fluid 1026 remains under pressure, elution fluid 1026 remains a liquid. However, when nozzle 1071 is opened, the pressure is released and elution fluid 1026 turns to foam. The foam then flows through nozzle 1071, into the device attached to elution cartridge 1070, and elutes filtered particles as described above.

Figure 11A:
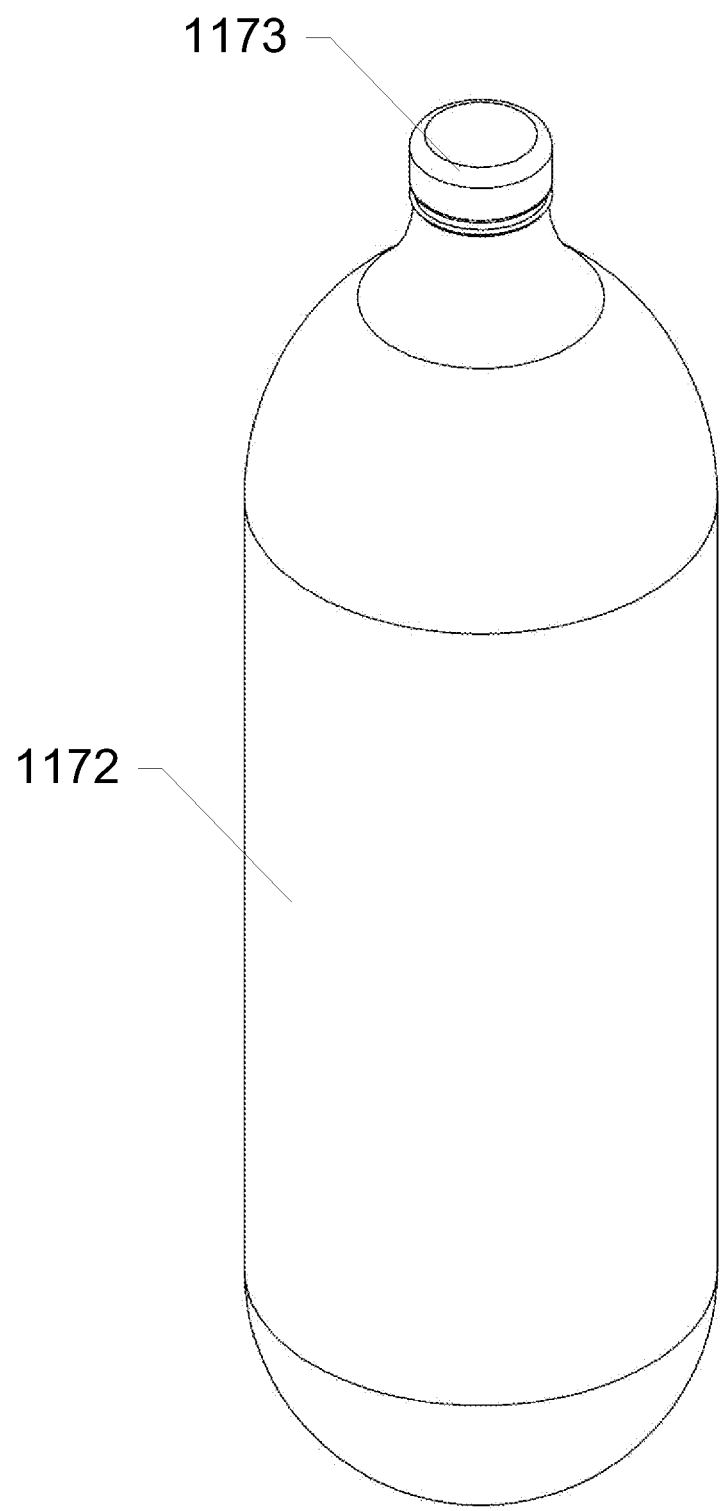

FIG. 11A shows an elution cartridge 1172, according to an exemplary embodiment of the present invention. Elution cartridge 1172 is used to elute particles from a filter of a device. In this embodiment, elution cartridge 1172 has rounded edges. Elution cartridge 1172 includes a nozzle 1173. Nozzle 1173 may be formed in many different configurations such that it may be used for different devices. For instance, elution cartridge 1172 may be used with an HHC, with a flat, depth filter elution assembly, etc. Elution cartridge 1172 may be designed for a single use, or for multiple uses. Elution cartridge 1172 may be refilled or replaced after it has been used. Similar to nozzle 1071 of FIGS. 10A-C, nozzle 1173 may be a puncture disk that screws or is pushed into a piercing fitting on a device. Alternatively, nozzle 1173 may be an on/off valve or a pressure release valve. Nozzle 1173 may further be a valve that releases a metered dose when pushed down onto a fitting. Thus, embodiments of nozzle 1173 allow for multiple extractions using the same elution cartridge 1172.

FIG. 11B shows a side view elution cartridge 1172, according to an exemplary embodiment of the present invention. Line A-A shows the cut through elution cartridge 1172 which produces the view shown in FIG. 11C.

FIG. 11C shows a cross-sectional view of elution cartridge 1172, according to an exemplary embodiment of the present invention. In this embodiment, the interior of elution cartridge 1172 holds an elution fluid 1126 and a compressed gas 1127. With the chamber under high pressure, compressed gas 1127 may dissolve into elution fluid 1126. As long as elution fluid 1126 remains under pressure, elution fluid 1126 remains a liquid. However, when nozzle 1173 is opened, the pressure is released and elution fluid 1126 turns to a foam. The foam then flows through nozzle 1173, into the device attached to elution cartridge 1172, and elutes filtered particles as described above.

Figure 12A:
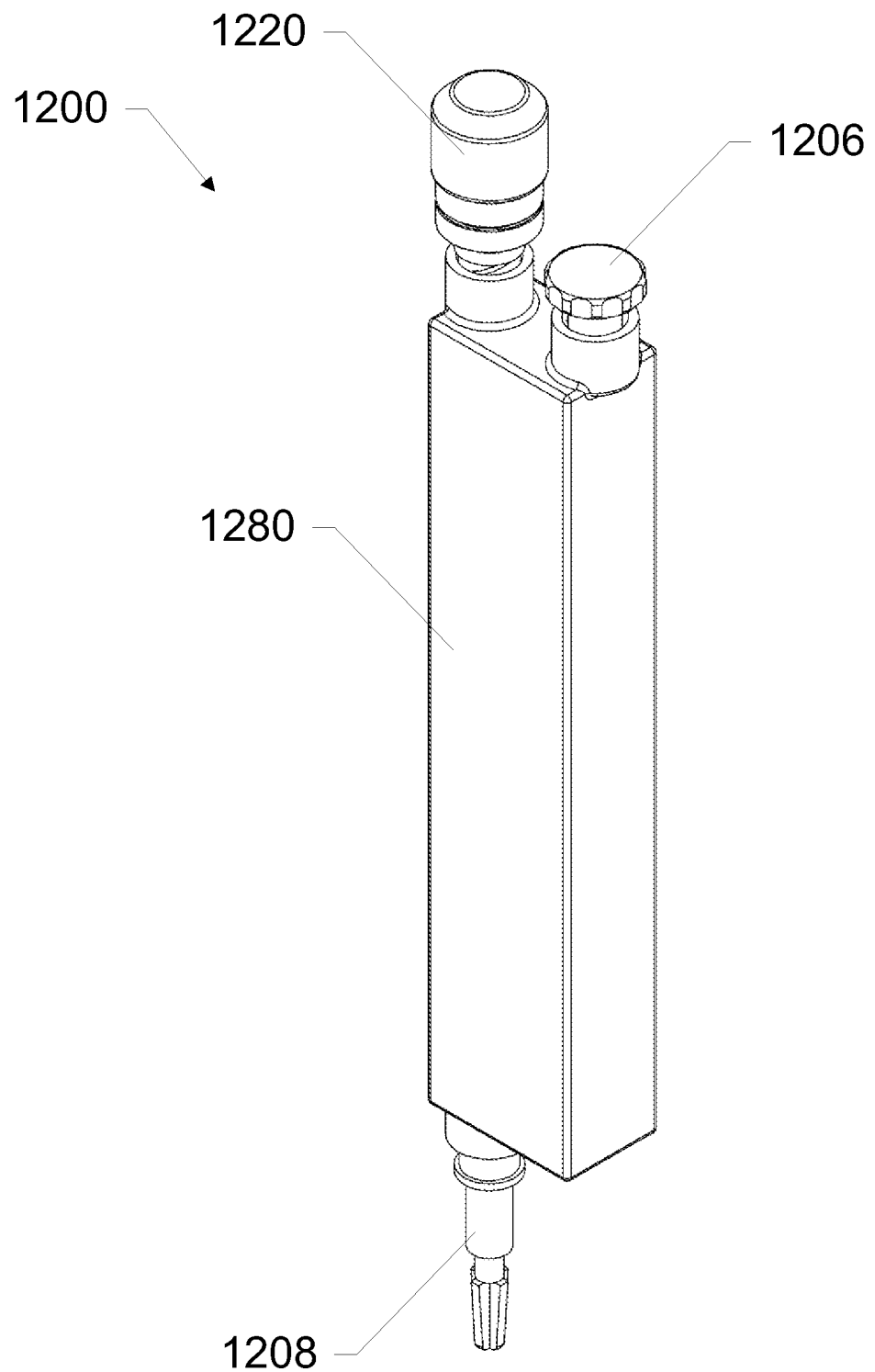
FIGS. 12A-C show a hand-held concentrator (HHC) utilizing a flat filter, according to an exemplary embodiment of the present invention.

FIG. 12A shows a hand-held concentrator (HHC) 1200 utilizing a flat filter, according to an exemplary embodiment of the present invention. In this embodiment, a body 1280 surrounds an internal chamber 1282 (shown in FIG. 12C). Body 1280 may be composed of any rigid or semi-rigid material. Body 1280 is preferably transparent such that a user can see the volume of a fluid sample that has been collected. Internal chamber 1282 may be sized such that it is larger than the fluid sample being collected. This sizing is such that when a vacuum is created in internal chamber 1282, the vacuum is able to draw the entire desired volume of the fluid sample. HHC 1200 further includes a filter, such as a flat filter 1215 (shown in FIG. 12C), an elution cartridge 1220, a tip 1208, and an evacuation port 1206.

Figures 12B, 12C:
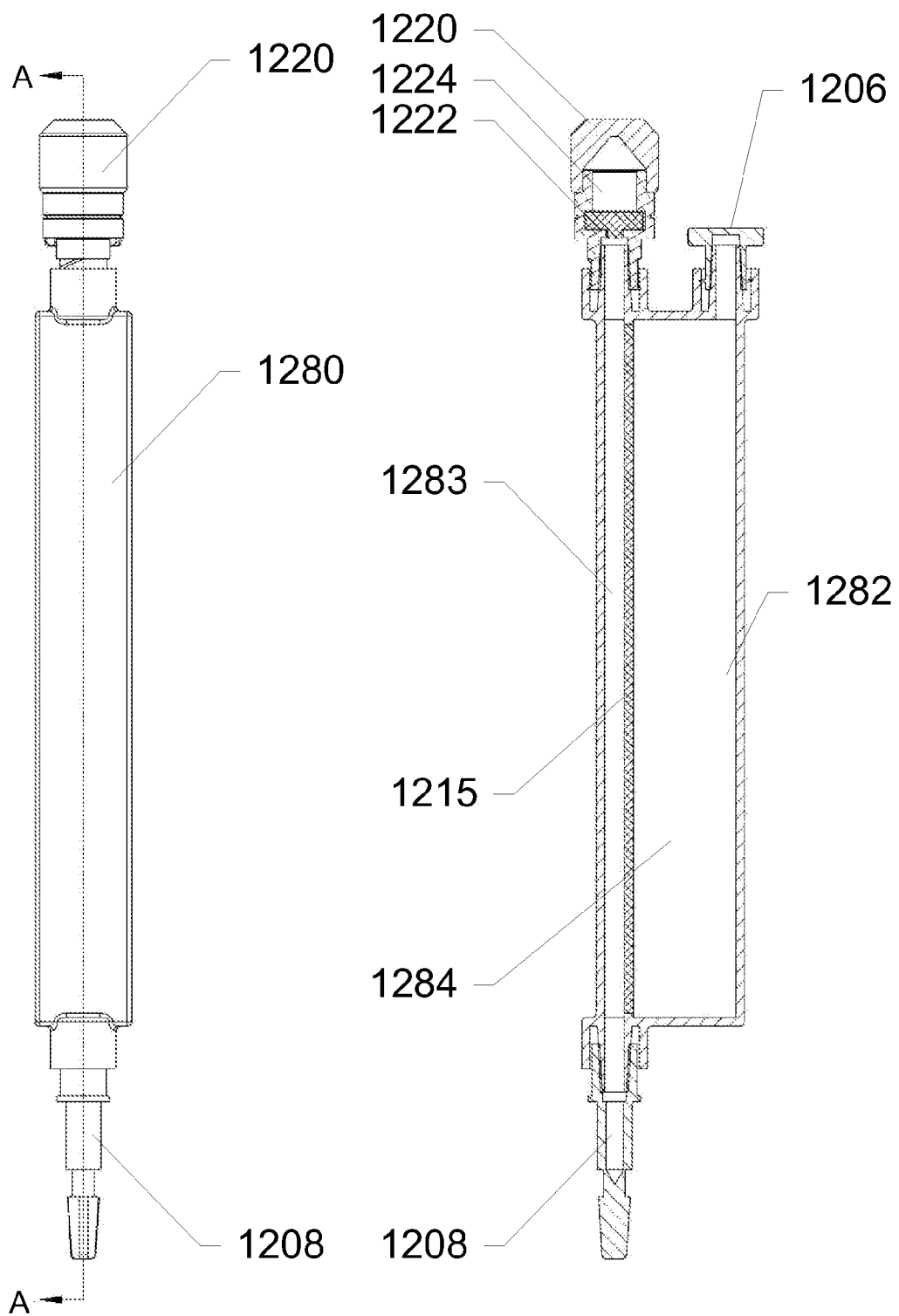

FIG. 12B shows a side view of HHC 1200, according to an exemplary embodiment of the present invention. In this embodiment, elution cartridge 1220 is aligned with tip 1208. Line A-A shows the cut through HHC 1200 which produces the view shown in FIG. 12C.

FIG. 12C shows a cross-sectional view of HHC 1200, according to an exemplary embodiment of the present invention. In this embodiment, HHC 1200 includes elution cartridge 1220 including an elution valve 1222 and an elution reservoir 1224, evacuation port 1206, internal chamber 1282, tip 1208, and a filter, such as flat filter 1215. Elution cartridge 1220 and tip 1208 are similar to previous embodiments. Flat filter 1215 is potted along the length of internal chamber 1282. Flat filter 1215 divides internal chamber 1282 into a retentate portion 1283 and a permeate portion 1284. Elution cartridge 1220 and tip 1208 are both aligned within retentate portion 1283 of internal chamber 1282. Evacuation port 1206 is located above permeate portion 1284 of internal chamber 1282. Evacuation port 1206 is used to create the vacuum inside internal chamber 1282. Evacuation port 1206 may also be used to release the vacuum from internal chamber 1282, for instance, when eluting particles from flat filter 1215.

With a vacuum created in internal chamber 1282 using evacuation port 1206; tip 1208 is placed in a fluid sample. Tip 1208 is removed or opened, opening the vacuum and drawing the fluid sample into retentate portion 1283 of internal chamber 1282, through flat filter 1215, and into permeate portion 1284 of internal chamber 1282, capturing target particles on the retentate side of flat filter 1215. Unwanted liquids/solutions and other particulates pass through flat filter 1215 into permeate portion 1284 of internal chamber 1282. When an appropriate volume of the fluid sample has been collected, HHC 1200 is lifted, thereby removing tip 1208 from the fluid sample. Elution cartridge 1220 is then manipulated by the user to open elution valve 1222 and release the elution fluid and gas combination from elution reservoir 1224. The elution fluid becomes a foam and elutes the target particles from flat filter 1215, by tangentially flushing the retentate side of flat filter 1215, sending the foam and target particles out of tip 1208, where the target particles may be collected.

The evacuation port may further be used to release any remaining vacuum after the desired amount of fluid has been sampled. This helps to prevent any of the elution fluid from being pulled into the permeate portion during elution, or to remove the fluid prior to elution.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A device for concentrating target particles from a fluid sample, the device comprising:
   an internal chamber;
   a filter within the internal chamber creating a retentate portion of the internal chamber and a permeate portion of the internal chamber, the filter having a porous surface;
   a tip in fluid communication with the retentate portion of the internal chamber;
   a drawing source within the internal chamber wherein the fluid sample is drawn by the drawing source into the tip and the retentate portion of the internal chamber, through the filter, and into the permeate portion of the internal chamber, and
   wherein target particles within the fluid sample are captured by the filter and
   an elution cartridge in fluid communication with the retentate portion of the internal chamber including a valve which opens when manipulated and releases an elution fluid to elute the target particles from the filter.

2. The device in claim 1, wherein the elution cartridge contains an elution fluid and a pressurized gas.

3. The device in claim 1, wherein the elution cartridge further comprises a breakable ampule, which, when broken, combines two reagents to create a gas.

4. The device in claim 1, wherein the drawing source is a vacuum in the internal chamber.

5. The device in claim 4, further comprising an evacuation port, wherein the vacuum is introduced through the evacuation port.

6. The device in claim 4, further comprising a second internal chamber in fluid communication with the internal chamber.

7. The device in claim 6, wherein the vacuum is created by a syringe coupled to the second internal chamber.

8. The device in claim 1, wherein the drawing source is an absorptive material.

9. The device in claim 1, wherein the filter is one or more of a plurality of hollow fiber filters, a flat membrane filter, a flat depth filter, an electrostatically charged filter, a zeta potential filter, and a microsieve.

10. The device in claim 1, wherein the tip is one of a breakaway tip, a capped tip, and a valve.

11. The device in claim 1, further comprising graduations on the internal chamber.

12. A method for concentration of target particles from a fluid sample, the method comprising:
    placing a tip of a hand-held concentrator in the fluid sample;
    opening the tip;
    drawing the fluid sample into the tip, through a filter, and into an internal chamber of the hand-held concentrator;
    capturing target particles from the fluid sample on the filter, wherein the fluid sample is drawn via a vacuum in the internal chamber, and
    eluting the target particles from the filter by manipulating a valve to release an elution solution from an elution cartridge.

13. The method of claim 12, wherein a syringe is used to create the vacuum.

14. A system for concentrating target particles from a fluid sample, the system comprising:
    a hand-held concentrator, the hand-held concentrator including an internal chamber, a filter within the internal chamber creating a retentate portion of the internal chamber and a permeate portion of the internal chamber, a tip in fluid communication with the retentate portion of the internal chamber, and a drawing source within the internal chamber; and
    an elution cartridge coupled to the hand-held concentrator, wherein the hand-held concentrator draws the fluid sample into the tip, through the retentate portion, and through the filter, capturing the target particles on the filter, and wherein the elution cartridge includes a valve which opens when manipulated and releases an elution fluid to elute the target particles from the filter.

15. The system of claim 14, wherein the drawing source is a vacuum within the internal chamber.

* * * * *